US012569537B2

(12) United States Patent
Newman et al.

(10) Patent No.: US 12,569,537 B2
(45) Date of Patent: Mar. 10, 2026

(54) SYSTEM AND METHOD FOR THE PRODUCTION, FORMULATION AND USE OF CONDITIONED MEDIA, CULTURED CELLS AND THE FACTORS INCLUDED THEREIN

(71) Applicant: Rinati Skin, LLC, Beverly Hills, CA (US)

(72) Inventors: Nathan Newman, Beverly Hills, CA (US); Alex Rajangam, Beverly Hills, CA (US); Dodanim Talavera-Adame, Beverly Hills, CA (US); Harpreet Sidhu, Beverly Hills, CA (US)

(73) Assignee: Rinati Skin, LLC, Beverly Hills, CA (US)

( * ) Notice: Subject to any disclaimer, the term of this patent is extended or adjusted under 35 U.S.C. 154(b) by 588 days.

(21) Appl. No.: 16/839,031

(22) Filed: Apr. 2, 2020

(65) Prior Publication Data

US 2020/0316169 A1 Oct. 8, 2020

Related U.S. Application Data

(63) Continuation-in-part of application No. 16/520,285, filed on Jul. 23, 2019, now Pat. No. 11,473,117.

(60) Provisional application No. 62/702,825, filed on Jul. 24, 2018.

(51) Int. Cl.

| | |
|---|---|
| A61K 38/17 | (2006.01) |
| A01H 4/00 | (2006.01) |
| A61K 9/00 | (2006.01) |
| A61K 38/20 | (2006.01) |
| A61K 38/21 | (2006.01) |
| C12N 5/077 | (2010.01) |
| C12N 5/0775 | (2010.01) |

(52) U.S. Cl.
CPC ......... *A61K 38/1709* (2013.01); *A01H 4/002* (2021.01); *A61K 9/0078* (2013.01); *A61K 38/2026* (2013.01); *A61K 38/204* (2013.01); *A61K 38/2066* (2013.01); *A61K 38/208* (2013.01); *C12N 5/0656* (2013.01); *C12N 5/0667* (2013.01); *A61K 38/2093* (2013.01); *A61K 38/217* (2013.01); *C12N 2500/76* (2013.01)

(58) Field of Classification Search
CPC .............. A61K 38/1709; A61K 9/0078; A61K 38/2026; A61K 38/204; A61K 38/2066; A61K 38/208; A01H 4/002; C12N 5/0656
See application file for complete search history.

(56) References Cited

U.S. PATENT DOCUMENTS

| | | | |
|---|---|---|---|
| 9,284,528 B2 | 3/2016 | Chuang et al. | |
| 2002/0164797 A1 | 11/2002 | Martin et al. | |
| 2004/0067920 A1* | 4/2004 | Leonard ............... | A61K 9/0075 |
| | | | 514/178 |
| 2012/0225029 A1 | 9/2012 | Al-Qahtani | |
| 2012/0301411 A1 | 11/2012 | Ludwig et al. | |
| 2015/0071877 A1 | 3/2015 | Maguire et al. | |
| 2015/0320801 A1* | 11/2015 | March .................... | A61K 35/28 |
| | | | 424/93.7 |
| 2018/0133138 A1 | 5/2018 | Exposito et al. | |

FOREIGN PATENT DOCUMENTS

| | | |
|---|---|---|
| EP | 2708596 B1 | 11/2016 |
| KR | 10-1570808 B1 | 11/2015 |
| WO | 2009/139581 A2 | 11/2009 |

OTHER PUBLICATIONS

Falk et al., Proc Am Thorac Soc, vol. 5, pp. 506-512, 2008 (Year: 2008).*
Nausch et al., PLOS One, Jan. 2013, vol. 8, issue 1, e54933, pp. 1-10 (Year: 2013).*
Razeghifard et al., Protein Expression & Purification, vol. 37 (2004) pp. 180-186 (Year: 2004).*
Dictionary.com Aspirate Definition & Meaning, retrieved from the internet Mar. 17, 2022: https://www.dictionary.com/browse/aspirate (Year: 2022).*
Mohammadipoor et al., Respiratory Research (2018) 19:218, pp. 1-14 (Year: 2018).*
Xu et al., Lancet Respir Med 2020; 8:420-22, published online Feb. 17, 2020 (Year: 2020).*
Chen et al., Stem Cell Research & Therapy (2015) 6:44, 12 pages (Year: 2015).*
Ferreira et al., Frontiers in Immunology, vol. 9, Article 2837, Dec. 2018, pp. 1-17 (Year: 2018).*
Vis et al., Frontiers in Bioengineering, vol. 8, Article 911, Aug. 2020, pp. 1-8 (Year: 2020).*
International Search Report and Written Opinion received for PCT Patent Application No. PCT/US2019/043314, mailed on Nov. 7, 2019, 10 pages.
Merriam-Webster definition of co-culture, retrieved from the internet Apr. 8, 2020: https://www.merriam-webster.com/dictionary/coculture (Year: 2020).
Pawitan, J.A., "Prospect of Stem Cell Conditioned Medium in Regenerative Medicine." BioMed Research International, 2014.
Raviraja, N.S. et al., "Stem Cell Derived Cosmetic Products: An Overview." Manipal Journal of Medical Sciences, 2016, p. 46-52, vol. 1, Issue 2.

(Continued)

*Primary Examiner* — Allison M Fox
*Assistant Examiner* — Hanan Isam Abuzeineh
(74) *Attorney, Agent, or Firm* — DLA Piper LLP (US)

(57) ABSTRACT

A technology regarding the production, formulation and use of conditioned media and the factors included therein is disclosed. The conditioned media may be inoculated with animal cells, plant cells and any combination thereof. The inoculations may occur simultaneous or at different times. Cells retrieved from different areas of the animal and/or the plant may also be cultured together to form conditioned media and associated growth factors.

17 Claims, 28 Drawing Sheets

(56) References Cited

OTHER PUBLICATIONS

Sello S. et al., "A Rapid and Efficient Method to Obtain Photosyn-
thetic Cell Suspension Cultures of *Arabidopsis thaliana*." Frontiers
in plant science, Aug. 18, 2019, pp. 1-8, v.8, No. 1444, Italy.
Aldag et al., "Skin rejuvenation using cosmetic products containing
growth factors, cytokines, and matrikines:a review of the literature",
Clinical, Cosmetic and Investigational Dermatology, 2016, 6(9):411-
419.

* cited by examiner

Consortia Media Scenario "1":
Sequential Co-culturing in Same Receptacle

Consortia Media Scenario "2":
Sequential Unidirectional System

Bidirectional Serial System

Cell Co-culture

Consortia Media

Unidirectional Loop System

Bidirectional Loop System

Additive Uni/Bi-directional System (a)

(b)

(c)

(d)

(e)

FACTOR PROFILES OF ASCs TREATED WITH
DEFINED OSTEOGENIC MEDIA VS. OSTEOGENIC CONSROTIA MEDIA

ASC treated with Defined Osteogenic Media

ASC treated with Osteogenic Consortia Media (a)

(b)

(c)

(d)

(e)

FACTOR PROFILES OF ASCs TREATED WITH
DEFINED CHONDROGENIC MEDIA VS. CHONDROGENIC CONSORTIA MEDIA

ASC treated with Define Chondrogenic Media

Cytokines

ASC treated with Chondrogenic Consortia Media

Cytokines (a)

(b)

(c)

(d)

(e)

a: Growth curve of flax cell culture b: Growth curve of Tulsi cell culture c: Co-culture of Flax and Tulsi

ASCs in SFBM + 10%HFCM

ASCs in LMS 2,4-D/KIN?
ASCs in LSM 2,4-D/KIN

CONSORTIA MEDIA FROM CELL-CELL INTERACTIONS
BETWEEN FLAX AND ADIPOSE STEM CELLS (a)

(b)

(c)

(d)

Table 1.

| ASCs co-cultured with Fibroblasts (preliminary) | | | | |
|---|---|---|---|---|
| Cytokine | ASC CSM | ASCs+Fib No-Contact (CSM) | ASCs+Fib Contact (CSM) | hF-CM (CSM) |
| 6Ckine | 10.57 | 16.16 | 10.69 | 4.88 |
| BCA-1 | 0.06 | 0 | 0.02 | 0 |
| CTACK | 0.37 | 0.49 | 0.07 | 0.86 |
| EGF | 0 | 0 | 0 | 0 |
| ENA-78 | 362.66 | 872.17 | 808.84 | 373.14 |
| Eotaxin-1 | 97.97 | 512.87 | 1384.92 | 2434.9 |
| Eotaxin-2 | 1.4 | 2.05 | 1.44 | 14.32 |
| Eotaxin-3 | 30.26 | 31.56 | 3.64 | 47.81 |
| FGF-2 | 13.07 | 21.91 | 24.82 | 20.27 |
| Flt-3L | 7.63 | 3.83 | 3.83 | 77.37 |
| Fractalkine | 26.25 | 23.11 | 14.05 | 14.69 |
| G-CSF | 1480.74 | 11.98 | 35.95 | 3.96 |
| GM-CSF | 7.64 | 2.13 | 1.98 | 1.98 |
| GRO alpha | 6352.04 | 1166.45 | 2580.8 | 3326.7 |
| I-309 | 2.29 | 0.53 | 0.23 | 0.31 |
| IL-10 | 0.93 | 0.68 | 0.61 | 0.8 |
| IL-12P40 | 3.92 | 0.88 | 3.07 | 2.31 |

FIG. 20

Table 1. (CONT.)

| MDC | 31.55 | 14.86 | 28.76 | 18.34 |
|---|---|---|---|---|
| MIP-1a | 26.11 | 16.97 | 0 | 11.67 |
| MIP-1B | 12.88 | 13.72 | 4.39 | 5.58 |
| MIP-1d | 1.18 | 1.94 | 1.33 | 1.33 |
| PDGF-BB | 1.73 | 3.25 | 0.84 | 4 |
| PDGF-AA | 12.06 | 0.25 | 0.17 | 1.54 |
| RANTES | 5858.76 | 152.46 | 122.55 | 425.03 |
| sCD40L | 0.22 | 0 | 0.15 | 0 |
| SCF | 1.23 | 4.51 | 6.14 | 7.78 |
| SDF-1a+B | 637.5 | 1603.35 | 958.87 | 756.67 |
| TARC | 0.13 | 0.37 | 0.11 | 0.17 |
| TGF-a | 0.3 | 0 | 0 | 0 |
| TNFa | 3.22 | 0.67 | 0.42 | 1.44 |
| TNFB | 0.05 | 0 | 0 | 0 |
| TPO | 18.98 | 45.17 | 10.69 | 18.26 |
| TRAIL | 0.17 | 0 | 0 | 0.17 |
| TSLP | 0.16 | 0.06 | 0.1 | 0.28 |
| VEGF-A | 143.79 | 212.96 | 5.74 | 92.57 |

FIG. 20 (cont.)

Table 2.

| | SFBM + 10%HFCM | | | LMS media | | |
|---|---|---|---|---|---|---|
| | Well #1 | Well #2 | Well #3 | Well #4 | Well #5 | Well #6 |
| Total # cells | $2.25 \times 10^5$ | $1.64 \times 10^6$ | $2.31 \times 10^5$ | $3.96 \times 10^5$ | $2.86 \times 10^5$ | $1.04 \times 10^6$ |
| # Live cells | $1.92 \times 10^5$ | $1.36 \times 10^5$ | $1.92 \times 10^5$ | $1.48 \times 10^5$ | $6.04 \times 10^4$ | $6.6 \times 10^4$ |
| % live | 85% | 83% | 83% | 38% | 21% | 6% |

FIG. 21

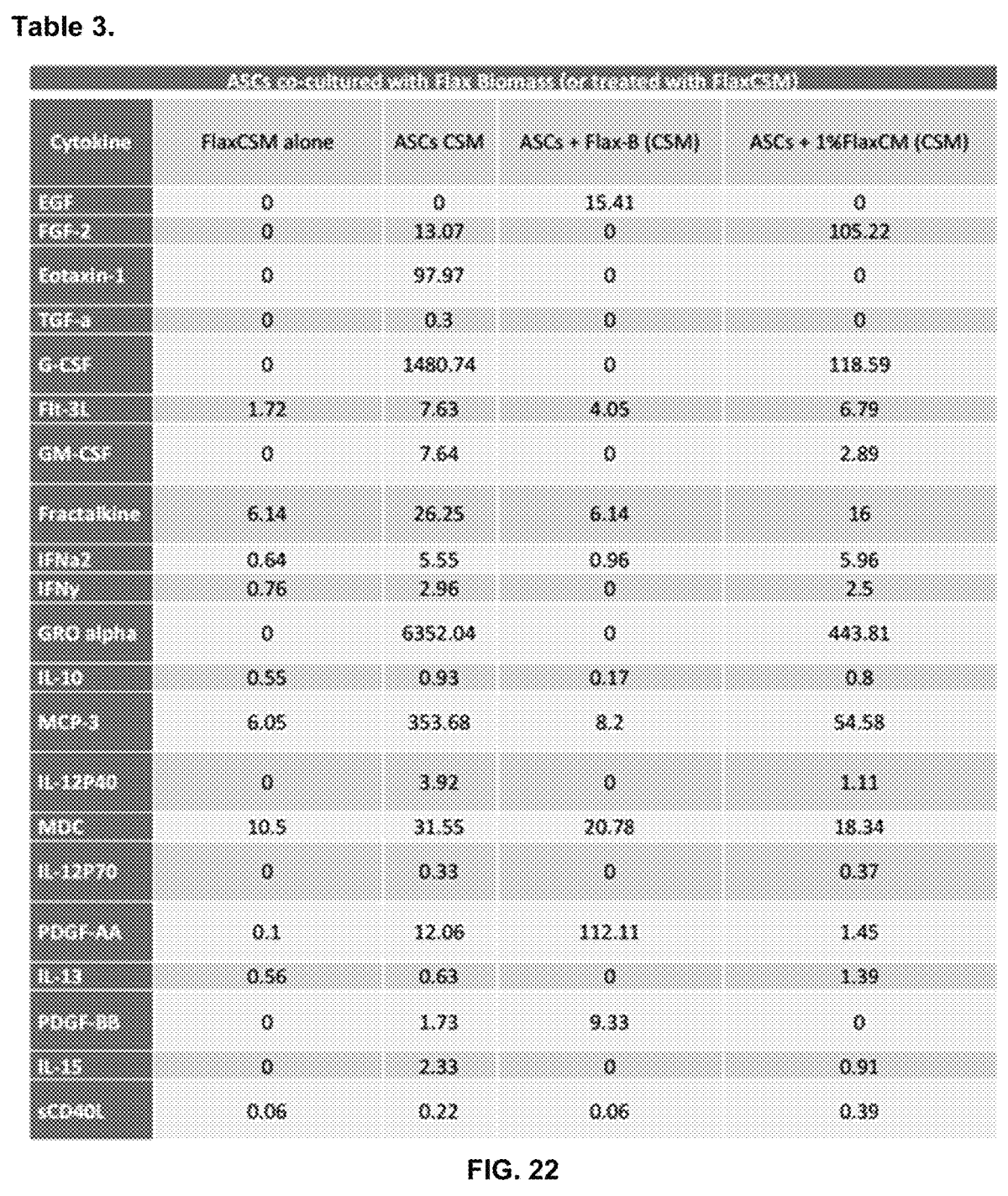

Table 3.

| Cytokine | FlaxCSM alone | ASCs CSM | ASCs + Flax-8 (CSM) | ASCs + 1%FlaxCM (CSM) |
|---|---|---|---|---|
| EGF | 0 | 0 | 15.41 | 0 |
| FGF-2 | 0 | 13.07 | 0 | 105.22 |
| Eotaxin 1 | 0 | 97.97 | 0 | 0 |
| TGF-a | 0 | 0.3 | 0 | 0 |
| G-CSF | 0 | 1480.74 | 0 | 118.59 |
| Flt-3L | 1.72 | 7.63 | 4.05 | 6.79 |
| GM-CSF | 0 | 7.64 | 0 | 2.89 |
| Fractalkine | 6.14 | 26.25 | 6.14 | 16 |
| IFNa2 | 0.64 | 5.55 | 0.96 | 5.96 |
| IFNγ | 0.76 | 2.96 | 0 | 2.5 |
| GRO alpha | 0 | 6352.04 | 0 | 443.81 |
| IL-10 | 0.55 | 0.93 | 0.17 | 0.8 |
| MCP-3 | 6.05 | 353.68 | 8.2 | 54.58 |
| IL-12P40 | 0 | 3.92 | 0 | 1.11 |
| MDC | 10.5 | 31.55 | 20.78 | 18.34 |
| IL-12P70 | 0 | 0.33 | 0 | 0.37 |
| PDGF-AA | 0.1 | 12.06 | 112.11 | 1.45 |
| IL-13 | 0.56 | 0.63 | 0 | 1.39 |
| PDGF-BB | 0 | 1.73 | 9.33 | 0 |
| IL-15 | 0 | 2.33 | 0 | 0.91 |
| sCD40L | 0.06 | 0.22 | 0.06 | 0.39 |

FIG. 22

Table 3. (CONT.)

| IL-17A | TT4 | 0.51 | 0 | TT7 |
|---|---|---|---|---|
| IL-1RA | 113.11 | 106.12 | 95.64 | 112.53 |
| IL-1a | 0 | 0.38 | 0 | 0 |
| IL-1b | 0.18 | 0.21 | 0.08 | 0.22 |
| IL-1b | 0 | 0.65 | 0 | 1.26 |
| IL-2 | 0 | 0.17 | 0 | 0.18 |
| IL-3 | 0 | 0.06 | 0 | 0.81 |
| IL-4 | 0 | 15.84 | 0 | 5.6 |
| IL-5 | 0.13 | 0.16 | 0.15 | 0.15 |
| IL-6 | 0 | 1027.34 | 0.05 | 327.27 |
| IL-7 | 0 | 2.77 | 0 | 2.35 |
| IL-8 | 6.58 | 9737.9 | 6.06 | 2453.14 |
| IP-10 | 0 | 193.63 | 0 | 42.15 |
| MCP-1 | 1.27 | 1737.6 | 30.85 | 7901 |
| MIP-1a | 0 | 26.11 | 0 | 6.98 |
| MIP-1b | 2.77 | 12.88 | 3.31 | 5.47 |
| RANTES | 1.38 | 5858.76 | 69.62 | 92.07 |
| TNFa | 0.05 | 3.22 | 0 | 3.91 |
| TNFb | 0 | 0.05 | 0 | 0 |
| VEGFA | 3.23 | 143.79 | 0 | 25.86 |
| GRO | 2.26 | 139.5 | 2.49 | 3.32 |
| Eotaxin2 | 0.2 | 1.4 | 7.48 | 0.97 |
| MCP-2 | 2.24 | 75.13 | 1.74 | 20.89 |
| CCL-1 | 0 | 0.08 | 0 | 0 |
| MCP-4 | 0.65 | 93.08 | 2.18 | 3.21 |
| IL-9 | 0.17 | 2.39 | 0.22 | 0.64 |
| IL-16 | 0 | 0.55 | 0 | 0 |
| TARC | 0 | 0.13 | 0.09 | 0 |
| CTACK | 0 | 10.57 | 0 | 0 |
| Eotaxin3 | 0 | 30.26 | 0 | 70.25 |

FIG. 22 (cont.)

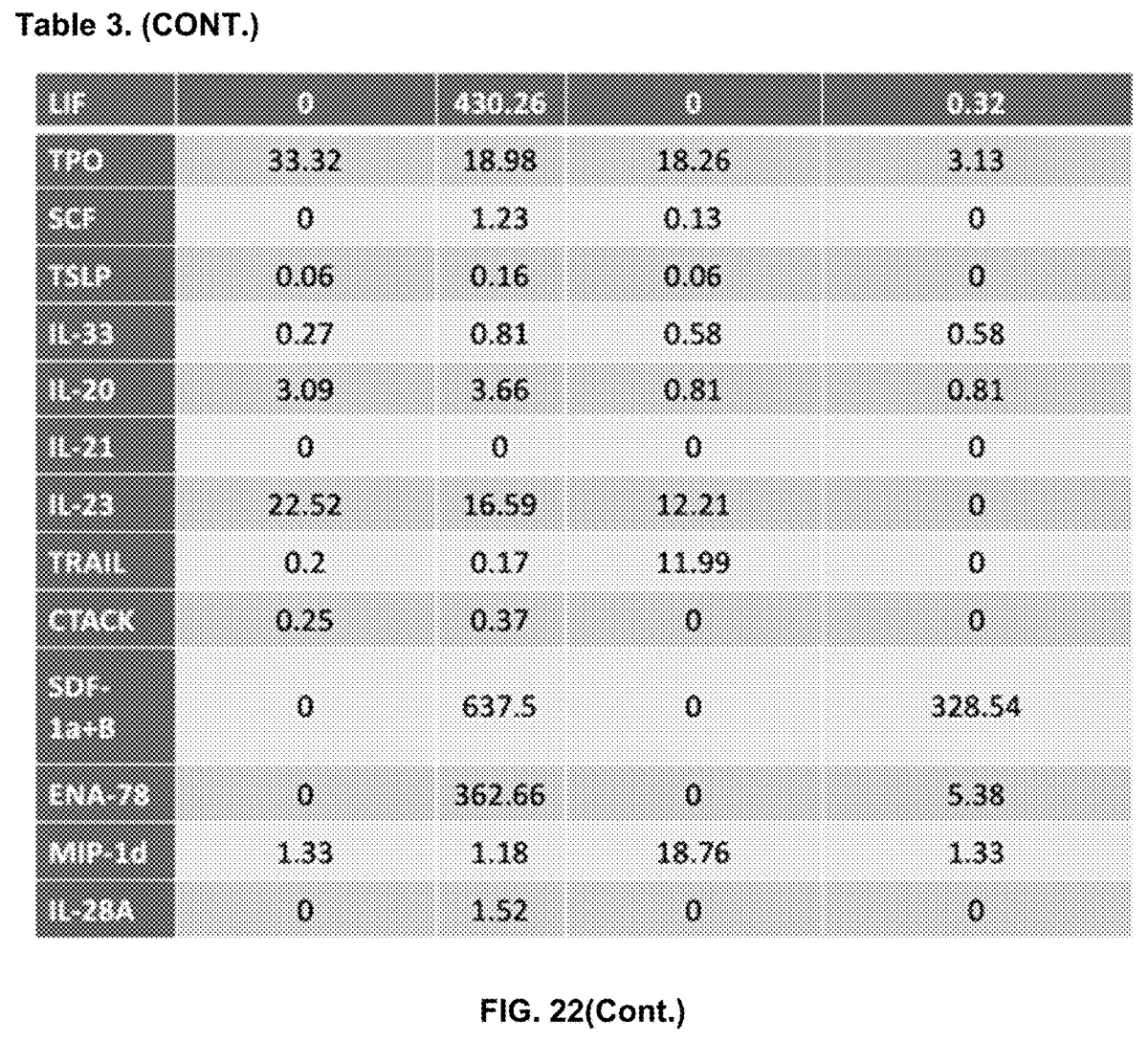

Table 3. (CONT.)

| LIF | 0 | 430.26 | 0 | 0.32 |
|---|---|---|---|---|
| TPO | 33.32 | 18.98 | 18.26 | 3.13 |
| SCF | 0 | 1.23 | 0.13 | 0 |
| TSLP | 0.06 | 0.16 | 0.06 | 0 |
| IL-33 | 0.27 | 0.81 | 0.58 | 0.58 |
| IL-20 | 3.09 | 3.66 | 0.81 | 0.81 |
| IL-21 | 0 | 0 | 0 | 0 |
| IL-23 | 22.52 | 16.59 | 12.21 | 0 |
| TRAIL | 0.2 | 0.17 | 11.99 | 0 |
| CTACK | 0.25 | 0.37 | 0 | 0 |
| SDF-1a+B | 0 | 637.5 | 0 | 328.54 |
| ENA-78 | 0 | 362.66 | 0 | 5.38 |
| MIP-1d | 1.33 | 1.18 | 18.76 | 1.33 |
| IL-28A | 0 | 1.52 | 0 | 0 |

FIG. 22(Cont.)

SYSTEM AND METHOD FOR THE PRODUCTION, FORMULATION AND USE OF CONDITIONED MEDIA, CULTURED CELLS AND THE FACTORS INCLUDED THEREIN

RELATIONSHIPS TO PRIOR APPLICATIONS

This application is a Continuation-In-Part of U.S. application Ser. No. 16/520,285 filed Jul. 23, 2019, which claims priority to U.S. Provisional Application No. 62/702,825, filed Jul. 24, 2018, the entire contents of which are hereby fully incorporated herein by reference for all purposes.

FIELD OF THE INVENTION

This invention relates to conditioned media and factors generated and included therein. More particularly, this invention relates to specifically designed conditioned media and factors, their formulation, their method of production and their methods and areas of use.

BACKGROUND

Most methodologies have been developed to maintain cells in culture. In parallel, several culture media with different composition have been formulated to culture and expand different cell types in vitro. Once the cells are isolated from their original niche, they start losing signals from their natural environment and change their phenotype. In order to maintain the original phenotype, complex culture media have been developed. However, some cells still lose some differentiation characteristics.

In these conditions, the cells produce extracellular matrix components that allow the cells to attach to the culture dish and establish physical contact with their neighboring cells. The cell-cell contact is important for cell-cell communication. However, there is another type of cell-cell communication through soluble factors that the cells release to communicate to other cells. These chemical communications have great impact on cellular behavior and function.

In vivo, the clearest example occurs during wound healing. When the skin is damaged, the epithelial cells in the epidermis and other cells such as fibroblasts and endothelial cells in the dermis respond immediately by releasing soluble factors to the closer environment and to the blood stream. These factors also provide signals to neighboring cells for further activation and differentiation.

In vitro, a similar process can take place, but the cell-cell interactions are limited to the culture dish area. Also, the factors released by cells grown in vitro are able to interact with specific membrane receptors and induce cell activation, migration, apoptosis, or differentiation. The in vitro system allows the detailed study of all these factors. Since these factors are released in the media where the cells are growing, it is possible to collect this media and analyze the profiles and levels of factors that the media contains.

It is also possible to manipulate the content of these media with different patterns of signals that can be introduced to the cells in culture. For example, vascular endothelial growth supplement (VEGS) is normally added to the media when endothelial cells are isolated for the first time (primary cultures). At present, the conditioned media derived from different cell lines has been analyzed and several factors including but not limited to, cytokines and chemokines, have been characterized. For example, Cytokines are peptides involved in cell-cell signaling with important physiological effects. They are able to regulate essential cellular functions such as cell division, growth, and death. Some of these factors have known important biological effects, which have been used in the treatment of several diseases.

Coronaviruses cause severe acute respiratory syndrome (SARS) in man. It has been suggested that the resulting pathology is not only a result of direct destruction of lung epithelia by the virus but from the release of secretory factors associated with persistent inflammation as well as white blood cell depletion leading to death. It has been shown that viral infection stimulates the cells to produce higher levels of secretory factors associated with inflammation, promoting an augmentation of the spaces between cells which leads to an increase in liquid transportation and promotes cell mobilization to the affected tissue.

SARS-CoV, including the novel coronavirus at the heart of the 2019-2020 outbreak, SARS-CoV-2, or COVID-19, can infect epithelial cells within the lung and other cell types such as macrophages and dendritic cells. Although these cells are able to contain/destroy viral particles in the early stages of the infection, they release secretory factors that may intensify subsequent inflammatory responses which in turn leads to a more severe disease state. For instance, it has been reported that inflammatory secretory factors such as IL-6 and IL-10 have been found in higher levels in the serum of patients infected by a SARS-CoV. In one of the fatal cases reported by Beijing, China, an exploration of the lungs revealed massive alveolar damage with respiratory failure and an accumulation of white blood cells with abundant viscous liquid. This patient was treated with an aerosolized form of the anti-viral/anti-inflammatory secretory factor interferon alfa-2b. Extensive studies have shown that some human stem cells can produce secretory factors with important anti-inflammatory effects.

This specification presents solutions to at least the following historical problems:

1. Selected factors are typically been used as chemicals at artificially created levels that do not simulate levels found naturally in the body. The physiologically imbalanced products are being used to treat disease but have been shown to cause severe, undesired side-effects in clinical settings.

2. No standardization process has been established to create a reproducible product using these secretory factors due to the lack of consistency in the profile.

3. No process in which the profile and/or patterns of signals/factors produced by the cells can be replicated with consistency for scalability.

As disclosed herein, this specification discloses novel solutions to the above presented problems in addition to other issues and problems not listed above. With this platform we are able to collect a set of factors that are chemically and physiologically balanced so that they may be used for therapeutic, medicinal and/or cosmetic purposes. This physiological balance may yield products that have the same or better results, without the undesired effects seen in the current methods. The process disclosed herein also provides a more efficient means of generating differentiated cells, including but not limited to, bone, hair, tissue, cartilage, and almost any other type of cell. The combination of factors, Consortia Factors as detailed herein, may be used for a variety of purposes both in vivo and in vitro.

SUMMARY OF THE INVENTION

The present invention is based on the seminal discovery that conditioned media and secreted factors included therein, and in particular the Consortia Media and Consortia Factors may be useful for a variety of therapeutic, medicinal and/or cosmetic purposes, and specifically for reducing inflammation and viral load, and for inducing tissue regeneration.

In one embodiment, the present invention provides a method for producing consortia factors from cells in a consortia media comprising: co-culturing in media, simultaneously or in successive inoculations, cells from a first source and cells from a second source, wherein the cells are cultured to produce a conditioned media. In one aspect, the first cells are stem cells and the second cells are fibroblasts. In one aspect, the factors include anti-viral factors and/or anti-inflammatory factors.

In another embodiment, the invention provides a pharmaceutical composition of consortia media comprising: a conditioned media and/or isolated factors produced by the method described herein. In one aspect, the pharmaceutical composition is formulated as a spray, lozenge, inhalation, or nebulization. In various aspects, the pharmaceutical composition is used for the treatment of a respiratory condition, wherein the respiratory condition is selected from the group consisting of asthma, chronic obstructive pulmonary disease (COPD), restrictive lung disease (RLD), sarcoidosis, severe acute respiratory syndrome (SARS), upper respiratory infection (URI), viral infections, influenza infection, coronavirus infection, emphysema and coronavirus-induced severe acute respiratory syndrome (SARS-CoV).

In a further embodiment, the invention provides a method of treating inflammation and/or coronavirus-induced severe acute respiratory syndrome (SARS-CoV) comprised of using an inhaler or a nebulizer that releases an aerosolized and/or nebulized pharmaceutical composition comprising a consortia media and/or isolated factors produced by cells. In many aspects, the SARS-CoV is caused by COVID-19. In various aspects, the aerosolized/nebulized pharmaceutical composition comprises anti-inflammatory factors consisting of interleukin (IL)-1 receptor antagonist (IL-1RA), IL-4, IL-6, IL-10, and IL-13, and/or anti-viral factors consisting of interferon (IFN)-$\alpha$2, IFN$\gamma$ and leukemia inhibitory factor (LIF).

In an additional embodiment, the invention provides a method of decreasing inflammation, decreasing viral load, and/or promoting tissue regeneration in a subject comprising administering to the subject an aerosolized pharmaceutical composition comprising a conditioned media and/or isolated factors produced by cells, wherein the subject has a coronavirus-induced severe acute respiratory syndrome (SARS-CoV).

BRIEF DESCRIPTION OF THE DRAWINGS

Various other objects, features and attendant advantages of the present invention will become fully appreciated as the same becomes better understood when considered in conjunction with the accompanying drawings, in which like reference characters designate the same or similar parts throughout the several views, and wherein:

Figures 18A, 18B, 18C, 18D:
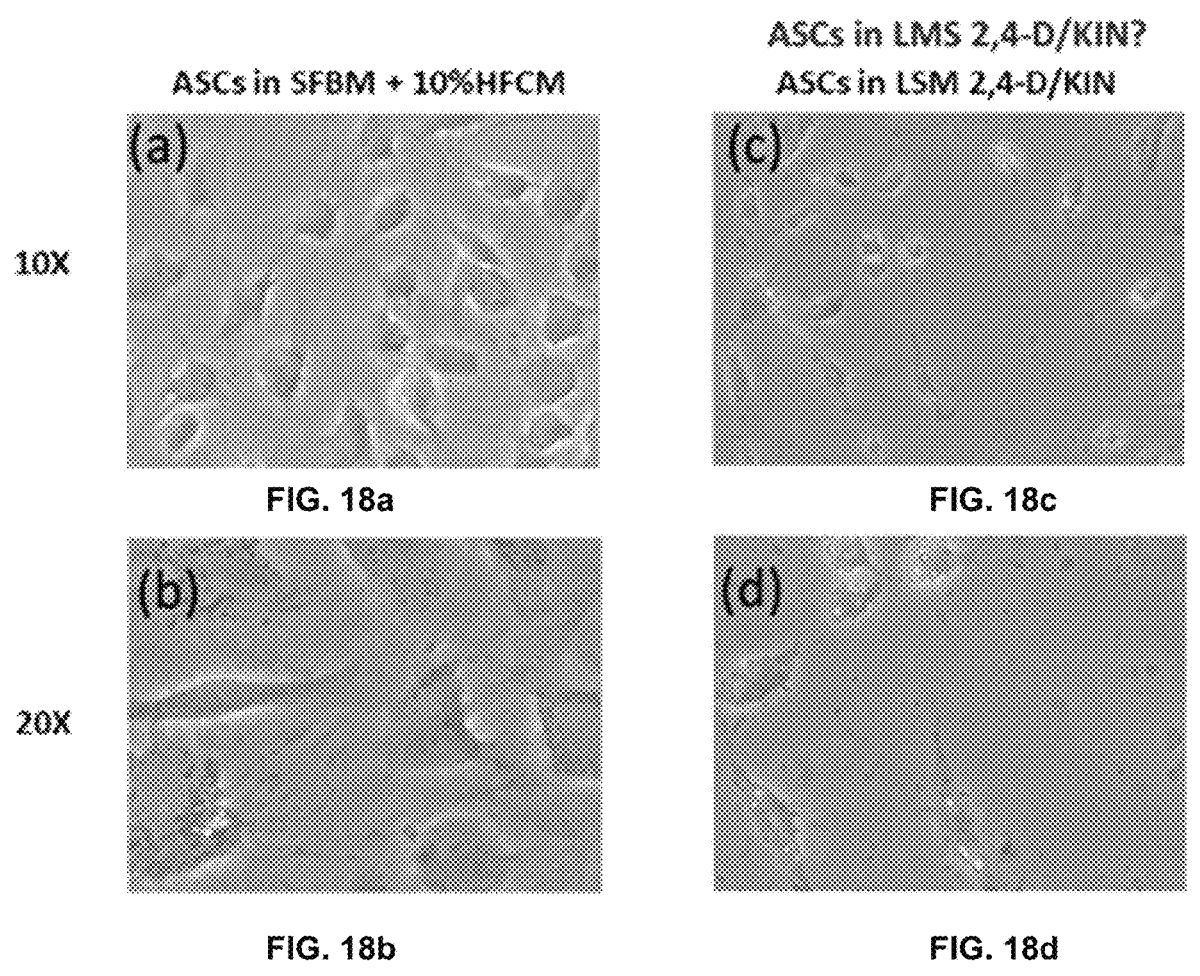

FIGS. 18a-18d show aspects of cell characteristics according to exemplary embodiments hereof.

FIG. 20 shows a table of factor profiles according to exemplary embodiments hereof.

FIG. 21 shows a table of cell characteristics in conditioned media according to exemplary embodiments hereof.

FIG. 22 shows a table of factor profiles according to exemplary embodiments hereof.

DETAILED DESCRIPTION OF EXEMPLARY EMBODIMENTS

Figure 1:
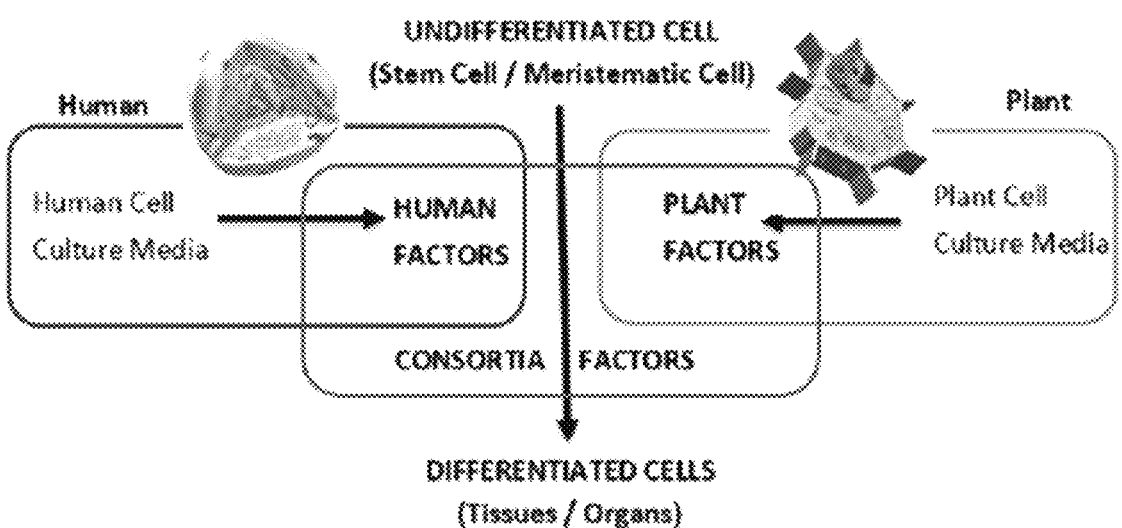
FIG. 1 shows aspects of cultured media, factors and differentiated cells according to exemplary embodiments hereof.

The following detailed description is not intended to limit the current invention. Alternate embodiments and variations of the subject matter described herein will be apparent to those skilled in the art.

This specification is organized into several main sections to facilitate the clear understanding of the novel subject matter described herein. These sections include:

I. Overview

II. Description of Novel Technologies and Developments

III. Support Information and Data

The Overview section provides an introduction and general overview of the novel technologies and developments described herein.

The Description of Novel Technologies and Developments section provides a detailed description of the novel systems, methods and new technologies that have been developed.

The Support Information and Data section provides detailed research, experimentation and production results that support the novel technologies and developments described herein. This section also includes methodologies that have been developed in accordance with the novel technologies.

I. Overview

Aspects of some exemplary embodiments and methods of the current invention include, without limitation, one or more novel conditioned media, a novel method to formulate and produce the conditioned media, novel factors and combinations of novel factors produced and/or included in the conditioned media, a novel method to produce and/or derive factors from the conditioned media, novel uses of the conditioned media, novel uses of the factors and combinations of factors obtained from the conditioned media, novel uses of the conditioned media and the factors included therein, as well as other aspects of the conditioned media, the factors included in the conditioned media, and other elements and characteristics of the conditioned media.

In some exemplary embodiments hereof, the conditioned media may include a cultured media conditioned with eukaryotic cells, human stem/stromal cells and/or human fibroblasts, animal stem cells, plant stem cells (e.g. meristematic cells), and/or any combination thereof cultured together, individually and/or in any combination. Additional details of the types of cells and/or combinations of cells will be provided in other sections.

The cells may grow in any system, including but not limited to, two and/or three-dimensional scaffolds using any form of suspension, traditionally a liquid/gel suspension and in a controlled static or dynamic system, such as spinner bottles and/or bioreactors. The invention describes the method to culture these cells in a controlled system to facilitate the establishment of effective cell-cell interactions and to collect the conditioned media that contains the various profiles of factors that may be used in vitro or in vivo for uses ranging from cosmetics, to pharmaceuticals, to agriculture.

One aspect of the invention is the method of co-culturing, simultaneously or in successive inoculations, animal cells such as adipose stem cells, derived from different donors, or the same donor but with stem cells taken from different locations on the body or taken at different times or with cells introduced at different passages. For example, when using human cells, the cells may be taken from different parts of the human body such as from the thigh and from the abdomen. In another example, the cells may be taken hours apart up to weeks apart depending on the growth rates and the types of cells. This novel methodology allows for unique cell-cell communication that promotes the secretion of soluble factors mimicking physiologically and chemically balanced levels and profiles. Additionally, the methodology optimizes cell-cell interactions allowing for scalability.

An additional aspect of the invention is the method of co-culturing, simultaneously or in successive inoculations, plant cells such as meristematic stem cells, derived from different plants, or the same plant but with cells taken from different locations on the plant or taken at different times or with cells introduced at different passages. For example, when using plant cells, the cells may be taken from different parts of the plant body such as from the root and from the shoot. In another example, the cells may be taken hours apart up to weeks apart depending on the growth rates and the types of cells. This novel methodology allows for unique cell-cell communication that promotes the secretion of soluble factors mimicking physiologically and chemically balanced levels and profiles. Additionally, the methodology optimizes cell-cell interactions allowing for scalability In addition to the co-culturing of animal cells with other animal cells, or plant cells with other plant cells, our method also allows for co-culturing, simultaneously or in successive inoculations, of the animal cells with plant cells.

Additionally, the combination of factors released by human stem cells that affect plant meristematic cells and factors released by plant meristematic cells that affect human cells, promotes the production of novel factors with relevant therapeutic effects. A representation of this is depicted in FIG. 1. (FIG. 1A. Human Factors produced from Human Adipose Derived Stem cells, fibroblast cells and other cell types, FIG. 1B. Plant Factors produced from differentiated cells (plant extracts and plant tissue culture extracts) and undifferentiated meristematic cells, FIG. 1C. Consortia Factors produced by (i) using plant factor/s in the human cell culture media and derive its resultant consortia factors produced by human cells and (ii) using co-culturing human and plant culture systems in loop and circulating plant factors to plant cell culture).

In general, it has been determined that the elements within the formulated conditioned media (as described above and herein) interact in a way that one element may regulate the factors secreted by the other element(s).

Our methodology enables not only the concentration of these factors in solution but also the ability to recover the media in sterile conditions suitable for the formulation of pharmaceutical products, cosmetic products, agricultural products and other applications and/or products.

As is known in the art, stem cells may be cultured by adding the cells to a media, often referred to as cultured media, that may include the nutrients necessary to support the cells as they grow and multiply. Culture media compositions may typically include essential amino acids, salts, vitamins, minerals, trace metals, sugars, lipids, nucleosides as well as other components and elements necessary for the cells' growth and development. Cell culture media attempts to supply the components necessary to meet the nutritional needs required to grow cells in a controlled, artificial and in vitro environment. Nutrient formulations, pH, and osmolarity may vary in accordance with parameters such as cell type, cell density, and the culture system employed. Once the culture media is incubated with cells, the culture media may be referred to as "spent" or "conditioned media.

As the cells grow, they may secrete a variety of cellular metabolites and secreted proteins, including, for example, biologically active growth factors, inflammatory mediators and other extracellular proteins. These secretions may be generally referred to as "factors" or "secretomes". In this way, the conditioned media may contain many of the original components of the media, as well as the secreted factors from the cells.

Much of the research in this field has been focused on the cultured stem cells themselves. The byproduct of the cells and the fluid in which they were cultured/grown (the conditioned media) is usually discarded. Other research has focused on the conditioned media. For example, some research has isolated particular factors in the conditioned media and separated them out. However, the subject matter described within this specification focuses on the cultured media in its totality. Rather than look at individual cell types or individual factors (which traditional methods may immortalize and then use) this technology focuses on the totality of the factors in a physiological balance, in a balance controlled to achieve specific outcomes (i.e. differentiation).

Prior research has discussed using conditioned media from human sourced cells. For example, the conditioned cell media compositions of prior work may be conditioned using any eukaryotic cell type. In some examples, the media may be conditioned by stromal cells, parenchymal cells, mesenchymal stem cells, liver reserve cells, neural stem cells, pancreatic stem cells, and/or embryonic stem cells. This is described in detail in U.S. Pat. No. 6,372,494, the entire contents of which are hereby fully incorporated herein by reference for all purposes.

The new work however, according to exemplary embodiments describe herein, may include conditioned media from plant cells, and/or conditioned media from a combination of plant cells and/or eukaryotic cells (including human and/or animal cells) together to create a new and unique conditioned media. For the purposes of this specification, this new conditioned media is referred to as "Consortia Media".

This specification describes a novel technology comprising the method of making and using the conditioned media with unique chemical compositions. The conditioned media may include any molecule/compound, including but not limited, to cytokines, peptides, chemokines, and other type of molecule(s)/complex, hereinafter collectively referred to as the "Consortia Factors". In order to produce Consortia Factors, other cells including but not limited to, eukaryotic cells, animal stem cells and/or fibroblasts and/or plant stem cells alone or in combination, are cultured in any and/or all dimensional constructs or scaffolds.

The Consortia Factors may be produced in different types of defined media and/or Consortia Media being used as culture media. The Consortia Media may be added into any cell culture system. The Consortia Factors may be derived from unique cell-to-cell interactions between animal cells (including human cells), plant cells and any combination thereof. The details of the types of cells and the types of combinations of cells used will be describe in detail in other sections.

The Consortia Factors may be secreted into the media and may be introduced into final products either in a liquid form, or other processed forms, such as powder, emulsion, frozen, etc. The products may include any delivery system, including but not limited to, injection, ingestion, or topical. Example resulting products may include human/animal cosmetics, biopharmaceutical products, nutritional products, agricultural products and applications, bio-energy applications and other products and/or applications.

As described above, the Consortia Media may include factors grown from multiple sources (plant, animal and/or any combination thereof). The growth factors derived from using these cells together, in what is best described as a consortium of factors, is unique. The Consortia Factors may facilitate and increase the expected physiological growth of the cells. The Consortia Factors may also create a uniformity of factor profiles both in content and amount, found in the Conditioned Media, whereas with traditional methods, such consistency may be very limited. In the immediate invention, the constitution of the consortia factors may be very repeatable and predictable across a multitude of similar cultures using similar cells.

Because the constitution, patterns and levels of the Consortia Factors are highly repeatable and standardizable, predefined "formulations" of Consortia Factors may be formed that may be used for different and specific purposes.

For example, in one exemplary embodiment hereof, the Consortia Media and/or Consortia Factors, individually or in any combination, may be produced as "formulations" that may be used to direct cells (in vivo and/or in vitro) to regenerate, differentiate, repair, replace and/or induce very specific desired eukaryotic cells. In this way, the formulations of Consortia Media and/or the Consortia Factors may be used to help bone, cartilage, muscle, skin, tendon, hair, tissue, and/or organs to repair and/or regenerate. This not only enhances the repair/regeneration of damaged cells but may shorten the length of time it takes for such repair/regeneration to occur.

In another exemplary embodiment hereof, the consortia media and consortia factors may also allow for the creation of agricultural products, without having to cultivate any plants.

In another exemplary embodiment hereof, a process has been created through which the conditioned media is reintegrated with fresh cultured media to create a new media in which the stem cells are cultured creating a new set of factors/profile of factors and again creating consistency in these factors and the conditioned media, thus creating Consortia Media. This process may be performed using various methods as described in other sections.

II. Description of Novel Technologies and Developments

In some exemplary embodiments hereof, this invention relates to factor profiles (Consortia Factors) that are released by cells into unique conditioned media (Consortia Media) after cell-to-cell interactions between (without limitation):

1) Animal cells (including, but not limited to, human cells) and other animal cells;
2) Animal cells and plant cells;
3) Plant cells and other plant cells; and/or
4) Any combination thereof.

These cells may grow in any culture including two or three-dimensional cultures. The novel methodology allows for the ability to standardize and customize the level and profile of factors released by these cell-to-cell interactions.

A culture media (also referred to as growth media) may include a liquid or gel designed to support the growth of cells. Culture media generally comprise an appropriate source of energy and compounds that may regulate the cell cycle while maintaining pH levels and osmolarity. A typical culture media may include nutrients, essential amino acids, vitamins, inorganic salts, glucose, minerals, serum and other elements necessary to promote the growth of cells in a controlled cultured environment. Once the culture media has been inoculated with the desired cells to be cultured, the combination of cells and culture media may be referred to as a conditioned media.

Cultured cells within a conditioned media may secrete factors that may include heterogeneous groups of proteins that may regulate the growth and differentiation of the cells.

In one exemplary embodiment hereof, a novel conditioned media may be formed by combining a conditioned media of a first type of cells (cells #1) with a conditioned media of a second type of cells (cells #2). Additional conditioned media including additional types of cells (cells #n) may also be added. For the purposes of this specification, the term Consortia Media may refer to the combination of two or more conditioned media. That is, a Consortia Media may consist of two or more distinct conditioned media (e.g., cultures of cells #1, cultures of cells #2, . . . cultures of cells #n) combined together.

Cells #1, cells #2, . . . cells #n may come from one or more sources (source #1, source #2, . . . source #n, respectively). In one exemplary embodiment hereof, the sources #n may be plant, animal and any combination thereof. For example, the consortia media may be formed using the following combinations of cells (without limitation):

1) Animal cells (cells #1) and other animal cells (cells #2);
2) Animal cells (cells #1) and plant cells (cells #2);
3) Plant cells (cells #1) and other plant cells (cells #2); and/or
4) Any combination thereof.

Note that an animal source may include a human source. The sources #n may be distinctly different sources and/or the sources #n may be a single source but with samples taken from different areas on the source (e.g., abdomen/thigh for human, roots/shoot for plants, etc.), at different time intervals (e.g., minutes apart, hours apart, days apart, weeks apart, etc.), using other variations and/or any combination thereof.

In another embodiment hereof, a novel conditioned media may be formed by co-culturing a first type of cells (cells #1) with a second type of cells (cells #2). Additional types of cells (cells #n) may also be added. For the purposes of this specification, in addition to the combination of two or more conditioned media, the term Consortia Media may refer to the conditioned media resulting from the aforementioned co-culturing of different types of cells.

For the purposes of this specification, conditioned media #1 may include culture media #1 inoculated with cells #1 taken from a source (e.g., from source #1), conditioned media #2 may include culture media #2 inoculated with cells #2 taken from a source (e.g., from source #2 or from a variation of source #1), and conditioned media #n may include culture media #n inoculated with cells #n taken from a source (e.g., from source #n or from a variation of other sources used). Note that any Source #n may be the same as any other Source #n, but taken at different times, from a different location on the source, using any other variation or any combination thereof. Alternatively, any Source #n may be a distinctly different source than any other Source #n.

Cells #1, #2, . . . #n may include without limitation:

1) Eukaryotic cells, animal (including but not limited to human, other mammals, avian, rodent, etc.) stem/stromal cells and/or animal fibroblasts, endothelial cells, Induced Pluripotent Stem cells (IPS cells) from different sources (whether from different places in a single animal donor's body, from a single animal donor taken from the same location but at a different date of sample collection, from multiple sources or from multiple animal donor bodies) growing in specific serum-free or serum-based culture/induction/differentiation media.

For example, co-culturing, simultaneously or in successive inoculations between, without limitation:
i. Animal cell & same Animal cell from successive inoculation times;
ii. Animal cell & same Animal cell from different locations on the animal from simultaneous inoculations;
iii. Animal cell & different Animal cell from simultaneous inoculation;
iv. Animal cell & different Animal cell from successive inoculations;

2) Different types of plant stem/meristematic cells from the initial plant embryonic stem cells (totipotent) in shoot apical meristem and root apical meristem (SAM and RAM respectively) and the plant stem/meristematic cells derived from the multipotent stem cells such as vascular cambium, individually or derived from multiple types of plant meristematic cells.

For example, between, without limitation:
i. Plant stem cell of a genus & plant stem cell of the same genus of successive inoculation times;
ii. Plant stem cell of a genus & plant stem cell of the same genus of simultaneous inoculation;
iii. Plant stem cell of genus 1 & plant stem cell of genus of #n simultaneous inoculation;
iv. Plant stem cell of genus 1 & plant stem cell of genus #n of successive inoculations.

3) Eukaryotic cells, animal stem/stromal cells and/or animal fibroblasts, endothelial cells, iPS cells (either from an individual donor or from multiple donors) and/or plant meristematic cells.
4) Eukaryotic cells, animal stem/stromal cells and/or animal fibroblasts, endothelial cells, and/or iPS cells that grow in the conditioned media derived from plant meristematic cells;
5) Plant meristematic cells that grow in the conditioned media derived from Eukaryotic cells, animal/human stem/stromal cells and/or animal/human fibroblasts, endothelial cells, and/or IPS cells.
6) Plant cells introduced into animal cultured media;
7) Other types or combinations of types of cells.
8) Co-culture(s) of any combinations derived from using one or more of the above cells and/or specific culture/induction/differentiation media.
9) Creating a system in which all of the above interact, and stimulate cell to cell interactions between the various cultures being grown, as describe in further detail herein below, so as to stimulate growth of new and additional growth factors creating a unique culture media that is the Consortia Media described herein.
10) The cell-cell interactions described herein above may occur through direct contact between the cells or using the culture media as a conduit for the cell-cell interactions.

In general, the process starts with cells being cultured in culture media. This culturing of cells can be done in one sequential co-culturing in the same receptacle, or in different receptacles and then integrated. The conditioned media from one set of cultured stem cells may be integrated with the conditioned media from other cultured cells (e.g., in the various combinations described above in 1-10). This combination may be performed in different ways for different results/types of Consortia Factors, including but not limited to: unilaterally in a directional flow; bidirectional Serial System, Bidirectional Loop System; Additive Uni/Bi-directional System; and, cell co-culturing to create the Consortia Media.

In one exemplary embodiment hereof, the process of creating consortia media and consortia factors may begin by taking cells of diverse sources and culturing them. The source of the cells may be taken from a multitude of scenarios, and the diversity of cell sources may facilitate the creation of Consortia Media and Consortia Factors. The diversity may come from harvesting different types of cells and conditioned media as described above.

Figure 6:
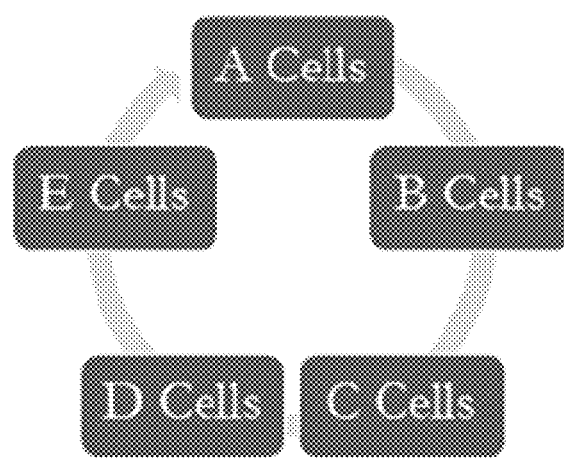
FIG. 6 shows aspects of a culturing technique using a unidirectional loop system.
Figure 7:
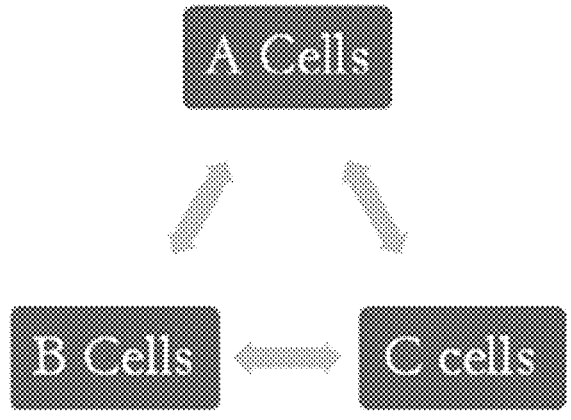
FIG. 7 shows aspects of a culturing technique using a bidirectional loop system.
Figure 8:
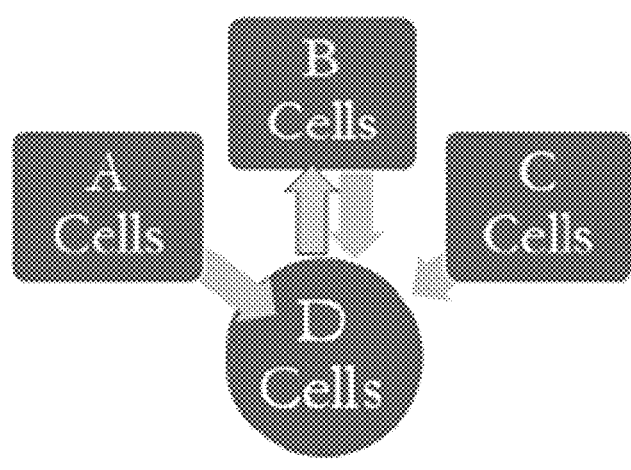
FIG. 8 shows aspects of a culturing technique using an additive uni/bidirectional system.

In another embodiment of the technology, the interaction of conditioned media #1, conditioned media #2, . . . conditioned media #n may be combined and/or formed in any manner of combination, including but not limited to the following scenarios: sequential co-culturing in the same receptacle (FIG. 2), sequential unidirectional system (FIG. 3), bidirectional serial system (FIG. 4), cell co-culture (FIG. 5), unidirectional loop system (FIG. 6), bidirectional loop system (FIG. 7), and/or additive uni/bi-directional system (FIG. 8). This interaction between the different conditioned media creates new forms of conditioned media with new factor profiles. This combined media and the resulting factors/factor profiles are Consortia Media and Consortia factors respectively.

In one example, cells #1 may be cultured in a culture media #1 to form a conditioned media #1, and cells #2 may be cultured in a culture media #2 to form a conditioned media #2. Then, the conditioned media #1 and the conditioned media #2 may be added together to form the overall conditioned media (the "Consortia Media")

In another example, cells #1 and cells #2 may be cultured in the same culture media (simultaneously or sequentially) to form the overall conditioned media (the "Consortia Media")

In addition, the media composition for the cell cultures may include, without limitation:

1) Cell culture media with serum;
2) Serum-free cell culture media;
3) Conditioned media as an additive to cell culture media;
4) Cultured media as cell culture media;
5) Consortia Media as an additive to cell culture media;
6) Consortia Media as cell culture media; and
7) Any other types of cell culture elements and/or any combination thereof.

In one exemplary embodiment hereof, once the consortia media is formed, the cells within the consortia media (cells #1, cells #2, . . . cells #n from possible source #1, source #2, . . . source #n) may interact with one another and secrete novel factor profiles. For the purpose of this specification, the novel factor profiles secreted by the cells within consortia media may be referred to as Consortia Factors. It is understood that two or more consortia media may be combined to form additional tiers of combined consortia media that may produce additional types of Consortia Factors. Further details and examples of this are described in Section III of this specification.

The consortia factors may include any molecule and/or compound, including but not limited to, cytokines, peptides, chemokines, and other type(s) of molecule(s) and/or complex(es) and any combination thereof. In order to produce consortia factors, animal stem cells (including human stem cells and/or stem cells from any known animal or being) and/or fibroblasts and/or plant stem cells alone or in combination may be cultured in any and/or all dimensional constructs or scaffold suspended in different types of defined and/or culture media (e.g. consortia media) added into cell cultures and/or bioreactors in a controlled growth cultured system, whether that system is a closed or open system.

Such systems create a platform in which any or all of the above interact. The interaction creates Consortia Media to be reintegrated into the process described or to create an interaction between them so as to stimulate growth of new and additional Consortia Factors. This in turn creates a new and unique Consortia Media different from those described herein above. The Consortia Media/Factors can also be used as a final product to be introduced into various other products for use/sale in the marketplace.

Traditionally, stem cells and/or the factors they produce, have been cultured with the goal of creating a specific "legacy" lines of cells or factors that may be reproduced with the goals that the specifically identified legacy cells/factors may treat specific health ailments or problems. The technology described herein fundamentally differs from that concept in a number of ways.

First, rather than looking for a legacy line of cells, the technology described herein uses the media in which the cells were cultured. In doing so, a "holistic" approach towards the factors is created that is more physiologically balanced and may thereby stimulate cells more effectively resulting in safer healing and regeneration.

Second, rather than looking at keeping a legacy line alive, the technology described herein creates effective cell-to-cell interactions between various types of cells as described herein, allowing for the factor profiles (peptides, non-protein growth factors, vitamins, fatty acids, extra nucleic acids, lipids, cytokines, small molecules, etc.,) aimed at a desired differentiation to be standardized.

Third, the technology described herein includes using a combination of plant meristematic cells and/or their conditioned media to create new factor profiles. Additionally, combination of plant meristematic cells with animal cells and/or their conditioned media can be used to create new factor profiles.

In one exemplary embodiment hereof, the cell-cell interactions as described herein may be optimized in a way to obtain combinatorial effects from the factors found in the conditioned media that may not exist otherwise. These cell-cell interactions may include cells at different culture stages and origins such as plant meristematic cells that grow with other meristematic cells from the same or different plant, and/or animal or human cells that grow with cell co-culturing to create the Consortia Factors and Consortia Media. Unlike prior uses of factors or media, the co-culturing that may create the Consortia Factors and Consortia Media demonstrates unique characteristics such as stability, consistency, repeatability in forming the desired Consortia Factors and desirable cellular effects unseen in prior art.

Co-culturing of different types of cells or of cells in different stages of differentiation has not been described, until now, in terms of their secretory products. It is this unique product that can be used in vivo or in vitro to direct a specifically desired effect on the cells.

The Consortia Media and/or the Consortia Factors, individually or in any combination, may be used in a wide range of applications including health products, biopharmaceutical products, personal care products, agricultural products and other products.

In one exemplary embodiment hereof, because the Consortia Media and/or Consortia Factors may be reproduced so efficiently, specific sets of "formulations" of media may be used to cultivate the stem cells, resulting in specific and consistent sets of factor profiles released. After cultivation, these formulations may contain standardized levels of biologically active secretory factors (Consortia Factors). These consistent sets of factors may then be used to increase the efficacy (in time and potency) of the differentiation.

Figure 9:
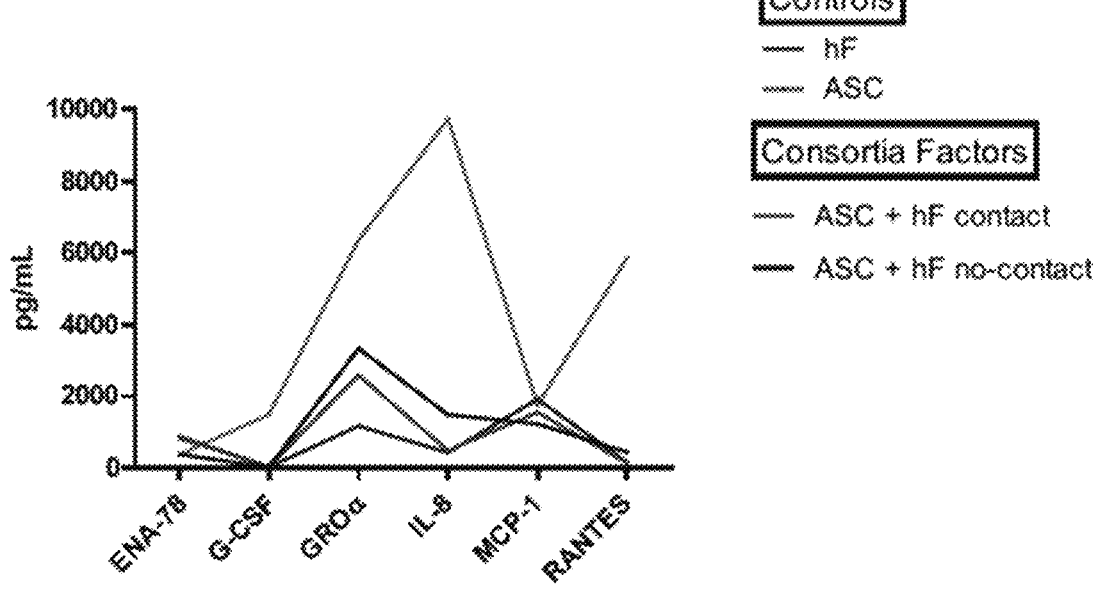
FIG. 9 shows aspects of conditioned media according to exemplary embodiments hereof.

The standardization of secretory factor levels may be quantified through a multitude of successive cell inoculations as described above, and then by quantifying the factor levels and patterns within each inoculation. That is, different types of Consortia Media may be used to form different types of Consortia Factors, and then the Consortia Media and Consortia Factors may be analyzed to determine their characteristics and compositions. Experimentation may continue until a desired Consortia Media and/or Consortia Factor is achieved, and then, since the results of this new technology of forming the media and/or the factors is so repeatable, standardization may be achieved. These cells may be inoculated into spinner bottles or bioreactors. This methodology alters the variations of the secretory factor profiles produced by the cells. It has been determined that this process is reproducible as is demonstrated with the embodiments referenced in FIG. 9. The descriptions and methodologies are described in detail in Section III of this specification.

The differentiations may occur either in vitro, or when introduced in vivo into the host (note that the host can be human, other animals, agriculture and/or any combination thereof). Each formula may be designed to stimulate a specific type of differentiation. For example, the formula for the media that may produce bone when applied to a patient may be different than the formula for the media that may produce hair. With these specific formulas applied to patients with specific needs, the recovery time for particular types of injuries may be greatly reduced. For example, the recovery time from broken bones may be reduced from months to weeks. This may also be used for other types of regenerative medicine ranging from organs to hair growth.

In further exemplary embodiments hereof, the Consortia Media and/or Consortia Factors, individually or in any combination, may be used to treat conditions such as dry eyes, psoriasis, eczema, auto immune diseases, alopecia, asthma, chronic obstructive pulmonary disease (COPD), restrictive lung disease (RLD), sarcoidosis, severe acute respiratory syndrome (SARS), upper respiratory infection (URI), viral infections such as influenza and coronavirus, emphysema and other conditions.

Since the differentiated cells may be reduced to liquid form, powder and/or gas, the delivery method of products that may include the Consortia Media and/or the Consortia Factors for health or other types of treatments may include injection, inhalation, topical, ophthalmic, otic, and/or ingestion as a distinct treatment and/or in any combination with other treatments. The Consortia Media and/or Consortia Factors, alone or in any combination, may be introduced into final products in liquid form, solid (frozen media, powder), gases/inhalants (e.g., micro-dispersion, dry powder inhaler, aerosol), other processed formats, other forms and any combination thereof.

In one exemplary embodiment hereof, the Consortia Media and/or Consortia Factors, individually or in any combination, may be used in formulations such as sprays, lozenges, inhalers, and nebulizers to treat symptoms of URI, asthma, RLD, COPD, SARS and other respiratory conditions. Pressurized metered-dose inhalers and nebulizers that release a fixed dose of aerosolized medication are widely used to treat respiratory diseases. For example, The SARS-CoV virus penetrates the respiratory system and may remain in the bronchial mucus and alveolar region until it finds a suitable lung cell (pneumocyte) surface to penetrate. In the clinical case reported, only one anti-viral secretory factor was used for treatment; however, other secreted anti-inflammatory factors or a combination of these should be used to decrease the rapid progression of the associated cellular damage and lymphocyte accumulation. These secretory factors can directly inhibit the virus and prevent the resulting massive cascade of pro-inflammatory effects. Hence, our Consortia Media and/or Consortia Factors is a strong candidate to treat SARS-CoV, and can be delivered in pressurized metered-dose inhalers or via nebulization to rapidly reach the affected mucosa to decrease inflammation, decrease-viral load and even promote tissue regeneration. In addition, it may be formulated as a spray or lozenge, for example, to reduce inflammation and help fight pathogens in the nares, mouth and throat and other mucosal tissues.

The Consortia Media and/or Consortia Factors, individually or in any combination, may also be used to treat similar conditions in other animals in addition to humans (e.g., dogs, cats, horses, etc.) by using similar methods as described.

In one exemplary embodiment hereof, the Consortia Media and/or Consortia Factors, individually or in any combination, may be used in agricultural applications. In one exemplary application, the Consortia Media and/or Consortia Factors may be used to cultivate and produce plant products without the need to cultivate the plants themselves. The benefits of this are multifold. First, this may allow for the ability to create food grade plant products using only a fraction of natural resources typically needed such as water, soil, nutrients and other resources. The food grade products may also be formed without the need for herbicides, pesticides, or other harmful components. In addition, the chemical and mineral content of the resulting products may be controlled, designed and/or manipulated.

In one example, plant meristematic cells may be used to differentiate the cells into any type of cell desired, and as such, the cells may be guided to grow into the cells that constitute a specific plant product. For example, it is known that oranges may be high in vitamin C. Traditionally, to get vitamin C from an orange, an entire orange tree must be grown that may provide the orange fruit. This process requires a great deal of water, soil and nutrients to grow the roots, trunk, leaves, branches and the orange. However, using the technology described herein, the cells that constitute the orange may be formed (differentiated) without the need for growing the tree. Note that the actual orange fruit may not necessarily be formed during the cellular differentiation, but instead, the cells that constitute the orange may be formed instead. Experimental examples of this are described in Section III of this specification with regards to flax and its health benefits. As described, the factors in flax which include the health benefits may be produced using this technology without growing the entire flax plant.

In another example, eucalyptus leave meristematic cells may be cultured and differentiated into the equivalent of the leaves. The essential oils and elements from those "leaf cells" may then be used for the health benefits they may provide, all without having grown a eucalyptus tree, which is notorious for the large amount of water it may take.

Additionally, the Consortia Factors may be grown with a consistent profile not subject to all the other influences traditional agriculture may be subject to. For example, grapes used for wine may have a different profile each year they are grown depending on the location, weather, soil, etc., all of which create inconsistencies within the grapes. This may be why a specific wine may have a distinctive and different taste from year to year, even though grown from the same seeds, in the same vineyard, with the same methodologies. However, by growing the cells, rather than the entire grape, these variables may be controlled to create a more uniform bouquet to the wine. Additionally, harmful pesticides, herbicides or other chemicals may be avoided.

In another example, the levels of vitamin "C" found in oranges may be increased. In another example, plants that may not typically include vitamin "C" may be grown such that they do. It can be seen that the growth of plant products without cultivation may also allow for growth of food products in environments that may not otherwise grow these foods.

As an additional benefit of the ability to cultivate plant materials without actual cultivation, this technology may induce photosynthesis, with minimal light, water, gases or other natural resources.

It is understood by a person of ordinary skill in the art, upon reading this specification, that any plant substance may be formed in this way, and that the scope of the invention is not limited in any way by the types of plant substances, media and/or factors that may be formed. For example, it is contemplated that the growth of substances like THC and CBD may be provided without the need for growing the actual plants. In this way, what may currently take acres of land to cultivate cannabis plants, may be done in a laboratory setting instead.

In addition to using the Consortia Media (and general conditioned media) for these products rather than discard it, the biomass from the media may include specific plant products that may allow the material to be formed as a food source and/or dietary supplement. Such food sources and/or dietary supplements may then be used in applications such as terraforming and space travel. The biomass may also be used for bio-diesel products and/or agricultural products (again with beneficial implications for terraforming and space travel). It is understood that not only may plant products be produced, but what would normally be considered waste in the industry, may also be formed into beneficial products.

For agricultural applications, the Consortia Media and/or the Consortia Factors may be delivered as additives to soil, as genetically engineered/modified plants or by other means.

It is understood by a person of ordinary skill in the art that the above examples are meant for demonstration and that the systems and methods described herein may be used to orchestrate other benefits within the fields of health, biotech, personal care, agriculture, cosmetics and other fields and applications, and that the scope of the systems and/or methods are not limited in any way by the fields into which they may be applied or by the benefits that they may provide.

III. Support Information and Data

Figure 4:
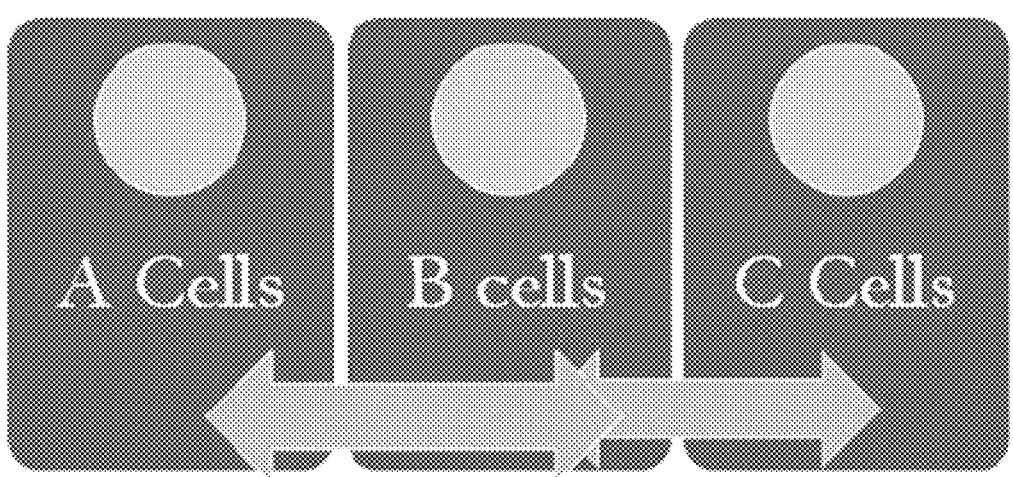
FIG. 4 shows aspects of a culturing technique using a bidirectional serial system.
Figure 5:
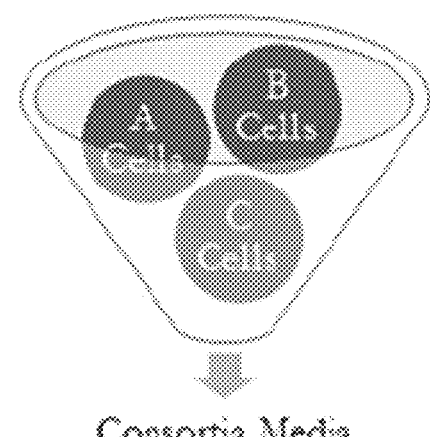
FIG. 5 shows aspects of a culturing technique using cell-co-culture.

Multiple experiments were performed, as detailed below, using two different methods when co-culturing cells. One without direct cell-cell contact and the other with direct cell-cell contact (FIGS. 4 and 5 respectively). The two resulting Consortia Media derived from these interactions were analyzed by cytokine multiplex analysis and compared to controls. (FIG. 9 and FIG. 20 (TABLE 1)). Table 1 shows cytokine multiplex analysis of consortia media (CSM) obtained from the interactions between human adipose stem and human fibroblast from different donors. In some co-cultures, there were no cell-cell contact (ASCs+hF No-Contact) and in another cultures, the cells were in contact (ASCs+hF Contact). The consortia media from Fibroblasts was also evaluated (hf-CM [CSM]). The values correspond to the cytokine level in pg/mL). The data demonstrates novel secretary factor profiles compared to controls. The pattern also demonstrated attenuated profiles of pro-inflammatory factors and chemokines. This has direct implications for pharmacological products.

Conditioned Media vs. Consortia Media Experiments

Adipose stem cells from the same donor were expanded and plated at high density in serum-free media. Chemically defined media was added to these cell cultures to promote differentiation to bone, cartilage and fat. After 20 days in culture, the cells were tested for differentiation. The remaining conditioned media recovered from the differentiation experiment was then used as culture media on ASCs. After 20 days in culture, the cells contained in the newly created Consortia Media were tested for differentiation. The profiles from the conditioned media and the Consortia Media were then analyzed. The results from each experiment are detailed below.

Conditioned Media from Defined Osteogenic Media vs. Osteogenic Consortia Media from Conditioned Media FIGS. 11a-11e show graphic representations and statistical analysis of one exemplary embodiment of the technology. The figures show secretory factor levels during differentiation of ASCs to bone, with 11(a) ASCs growing in SFM, 11(b) ASCs treated with growth factors (GF) to induce bone differentiation, 11(c) ASCs treated with Osteogenic Conditioned Media to induce bone differentiation, 11(d) Statistical analysis showing significant differences between the level of factors from ASCs growing in SFM vs ASCs treated with growth factors, and 11(e) Statistical analysis showing significant differences between the level of factors from conditioned media of ASCs growing in SFM vs. Consortia Media of ASCs treated with Osteogenic Conditioned Media. The results are taken from three independent experiments using Pairwise t-tests (P value).

Figures 10A, 10B, 10C, 10D:
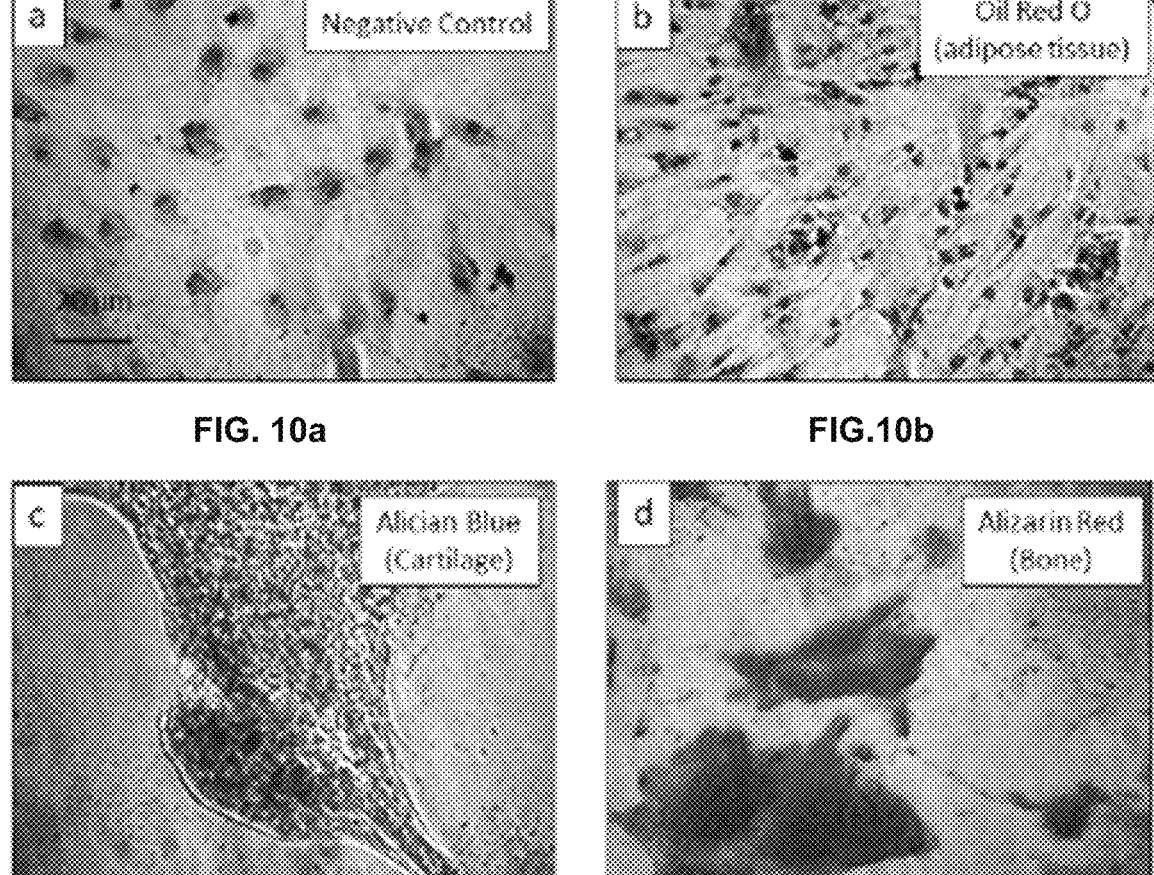
FIGS. 10a-10d show aspects of cell differentiation according to exemplary embodiments hereof.
Figure 11A:
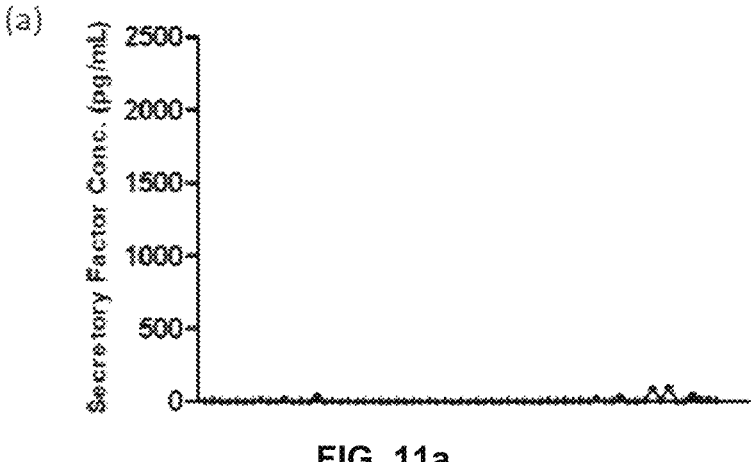
FIGS. 11a-11e show aspects of secretory factor levels according to exemplary embodiments hereof.
Figure 11B:
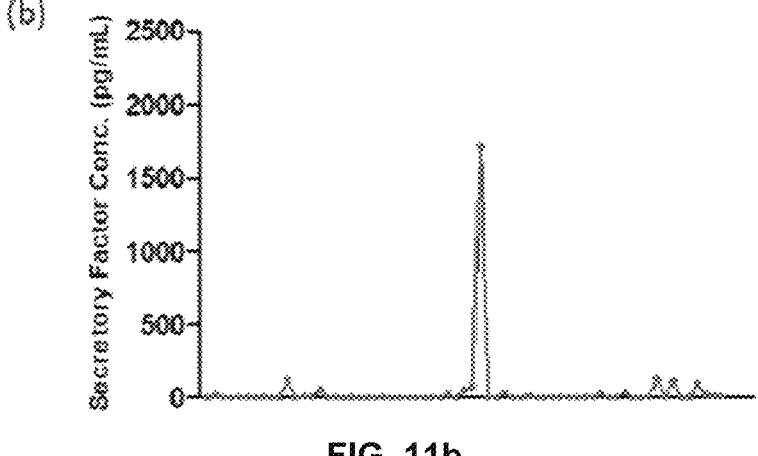
Figure 11C:
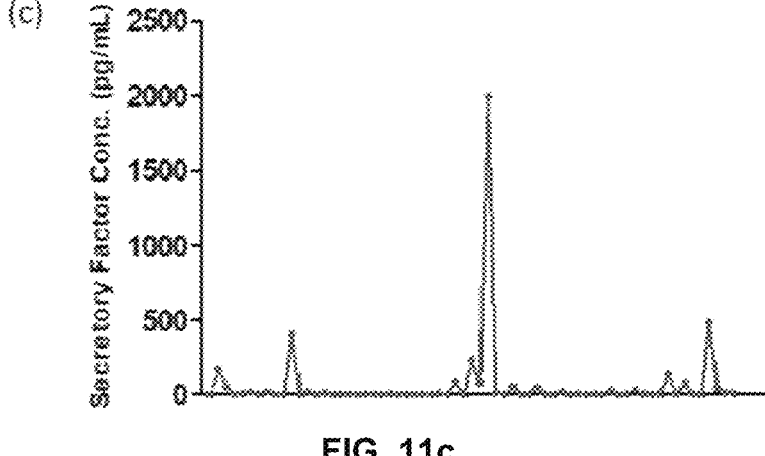
Figure 11D:
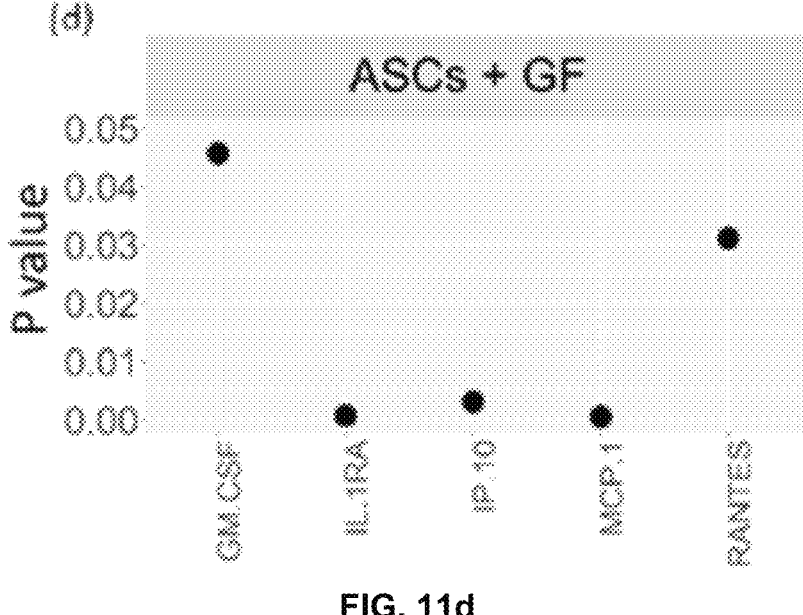
Figure 11E:
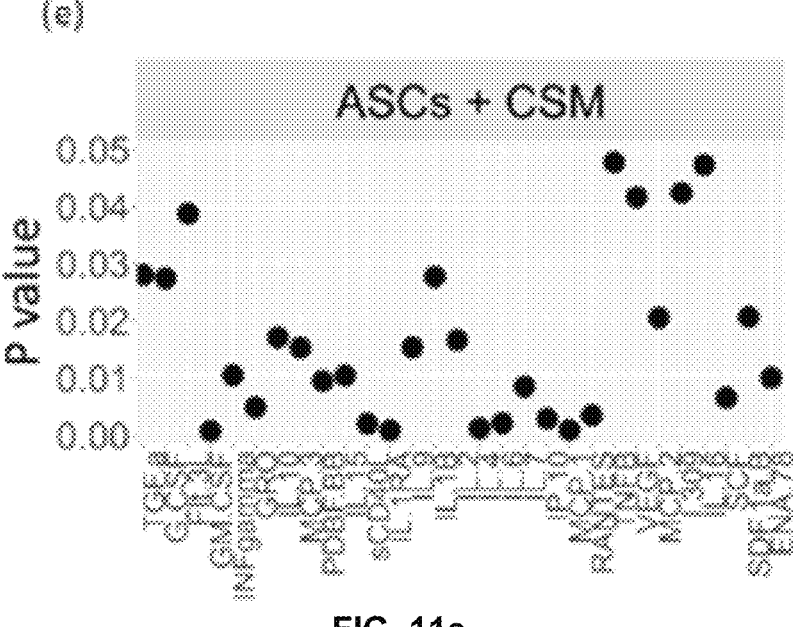
Figure 12:
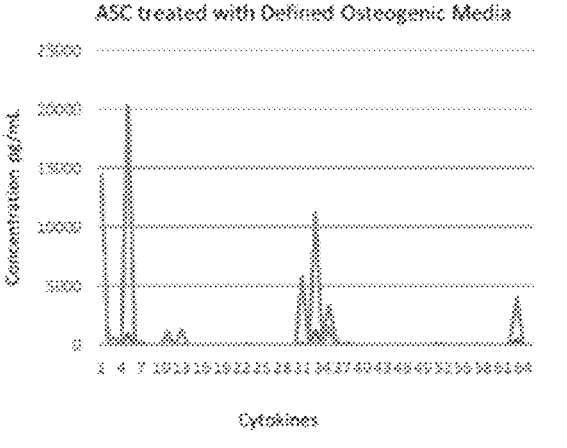
FIG. 12 shows aspects of aspects of factor levels according to exemplary embodiments hereof.
Figure 12:
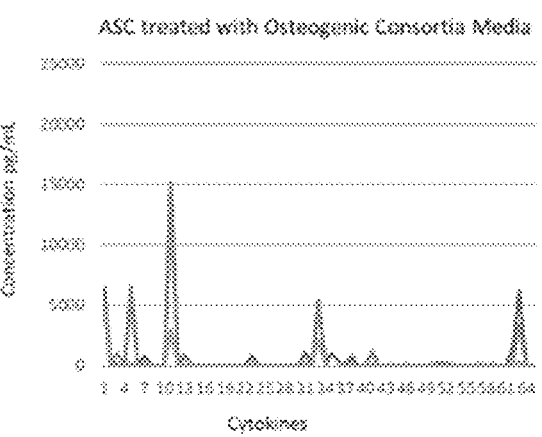
Figure 13A:
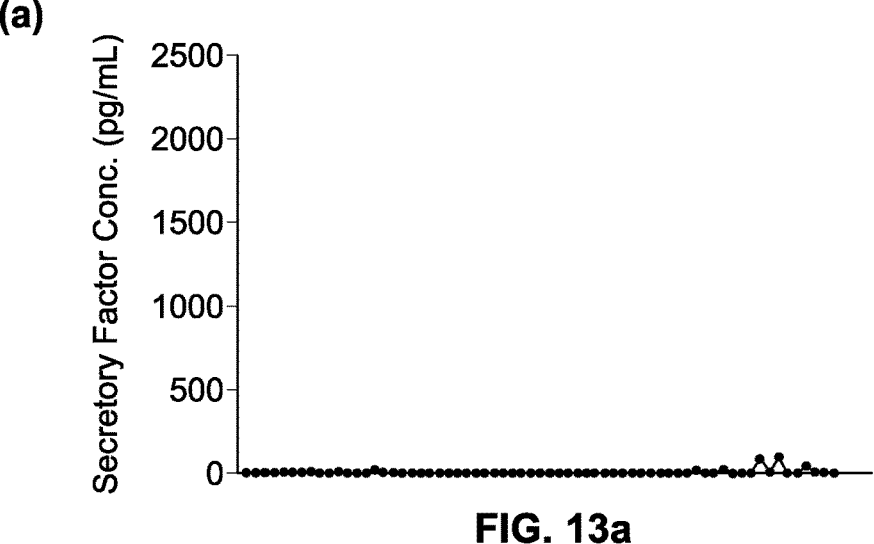
FIGS. 13a-13e show aspects of secretory factor levels according to exemplary embodiments hereof.
Figure 13B:
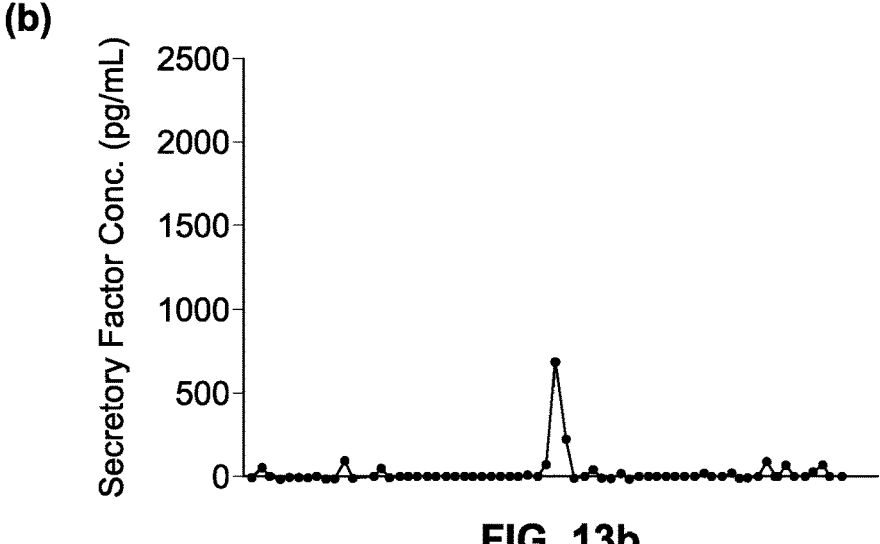
Figure 13C:
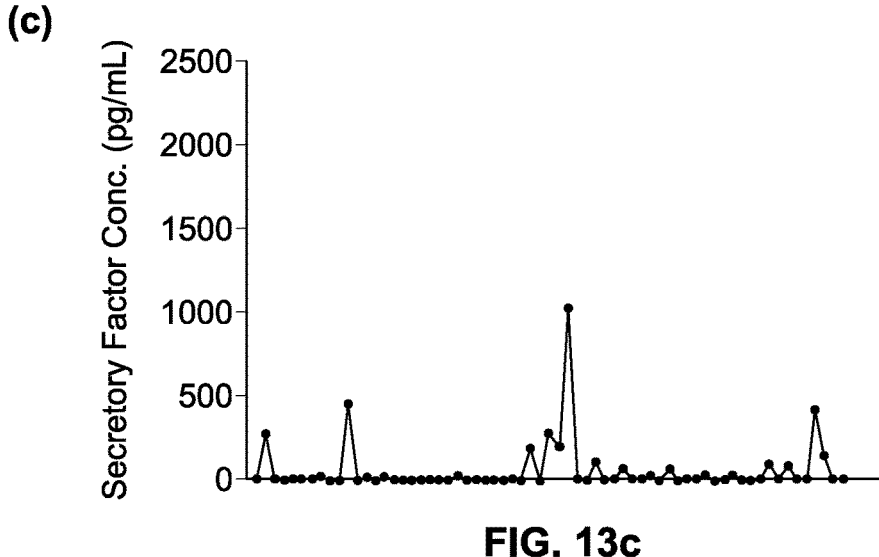
Figure 13D:
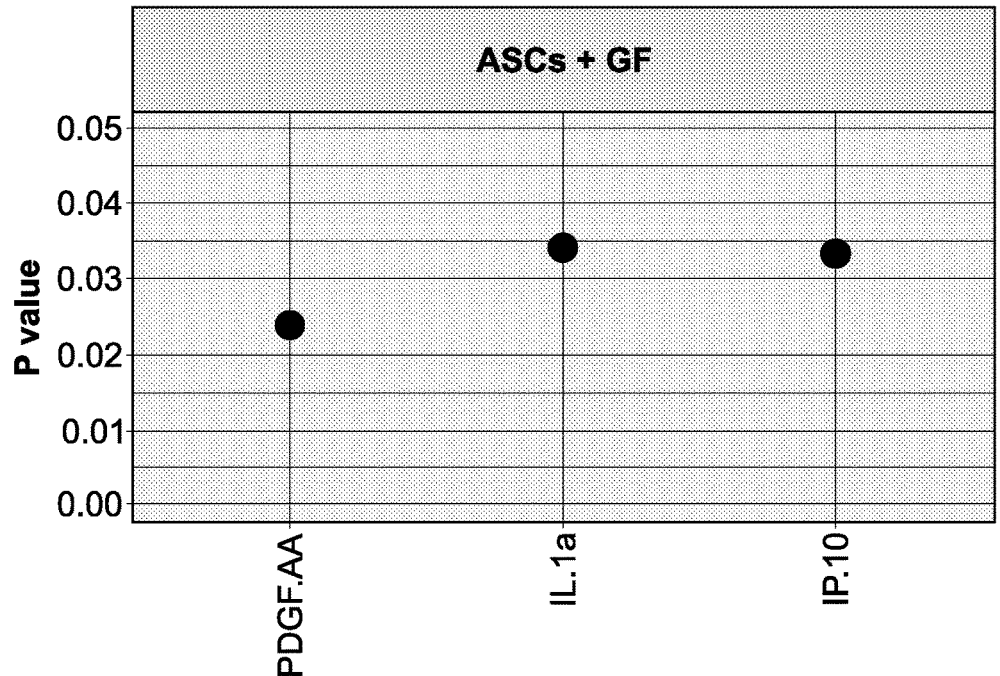
Figure 13E:
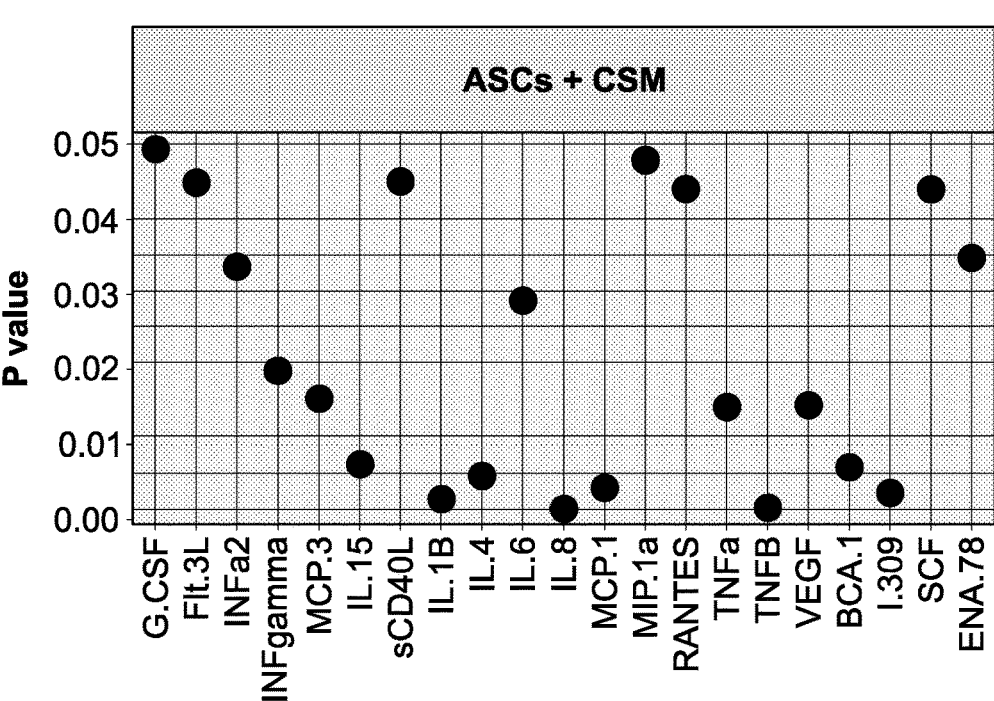

FIG. 12 factor profiles of ASC's treated with Defined Osteogenic Media versus Osteogenic Conditioned Media, demonstrates one exemplary embodiment of the novel technology. In this exemplary embodiment, the data demonstrates that this novel approach provides a consistent, reproducible set of factors for differentiation into bone. This Osteogenic Consortia Media shows an enhancement of the differentiation process (FIGS. 10a, 10d).

Conditioned Media from Defined Chondrogenic Media vs. Chondrogenic Consortia Media from Conditioned Media FIGS. 13a-13e show graphic representations and statistical analysis of one exemplary embodiment of the technology. The figures show secretory factor levels during differentiation of ASCs to cartilage, with 13(a) ASCs growing in SFM, 13(b) ASCs treated with growth factors (GF) to induce cartilage differentiation, 13(c) ASCs treated with Chondrogenic Consortia Media to induce cartilage differentiation, 13(d) Statistical analysis showing significant differences between the level of factors from ASCs growing in SFM vs ASCs treated with growth factors, and 13(e) Statistical analysis showing significant differences between the level of factors from conditioned media of ASCs growing in SFM vs. Consortia Media of ASCs treated with Chondrogenic Conditioned Media. The results are taken from three independent experiments using Pairwise t-tests (P value).

Figure 14:
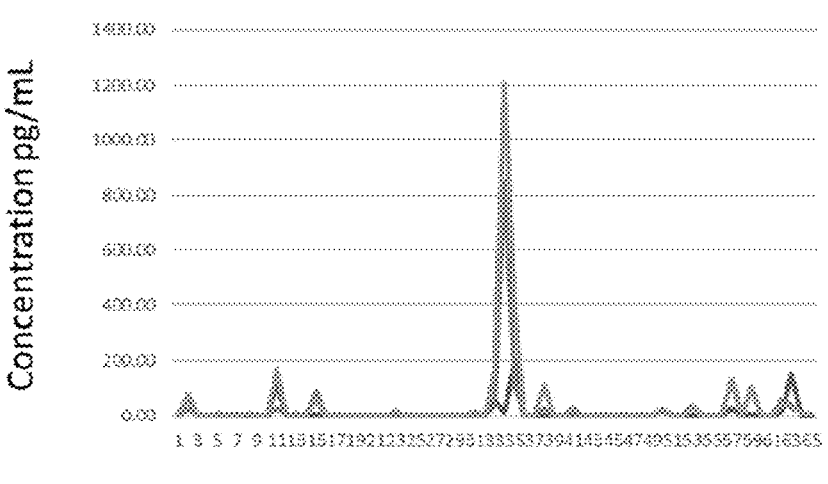
FIG. 14 shows aspects of aspects of factor levels according to exemplary embodiments hereof.
Figure 14:
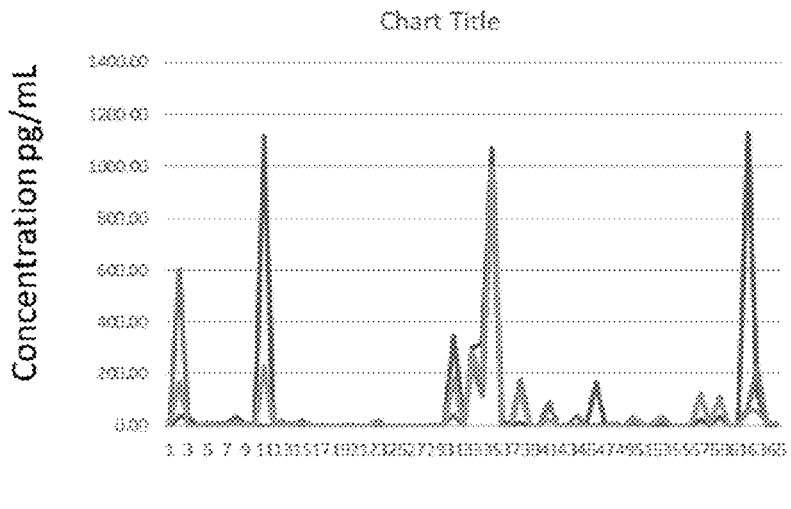
Figure 15A:
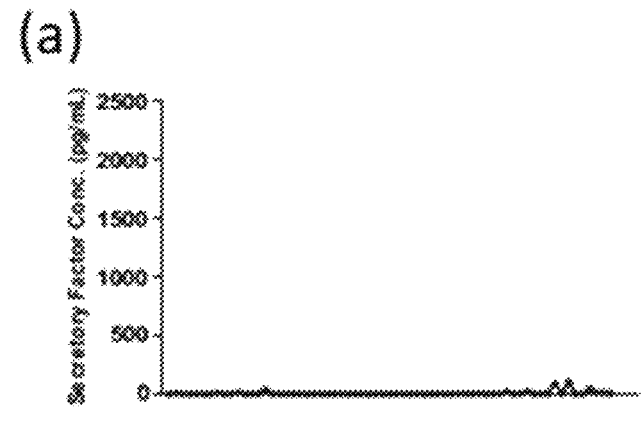
FIGS. 15a-15e show aspects of secretory factor levels according to exemplary embodiments hereof.
Figure 15B:
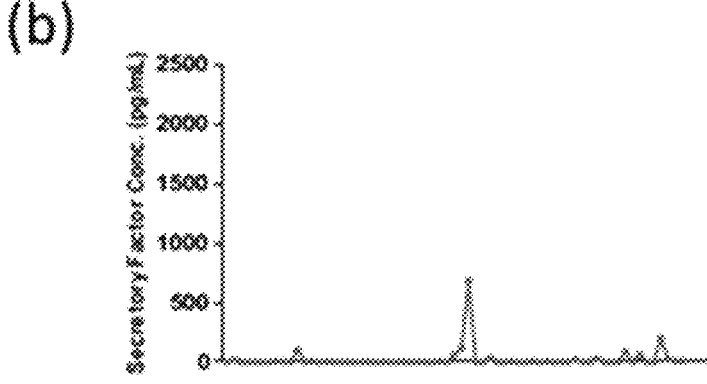
Figure 15C:
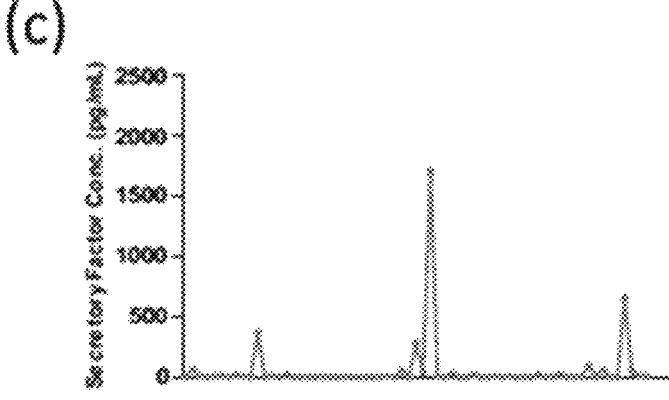
Figure 15D:
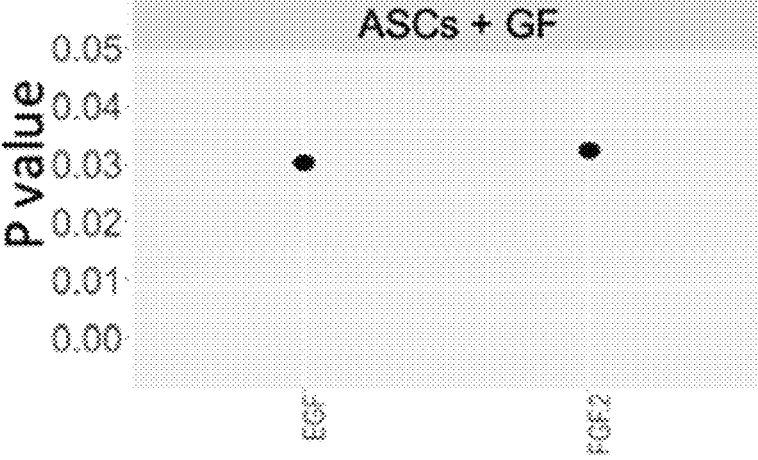
Figure 15E:
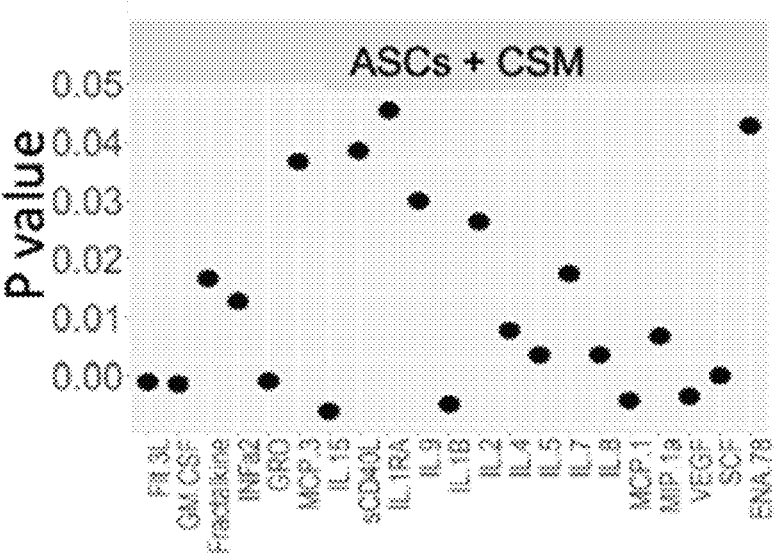

FIG. 14 shows Factor Profiles of ASC's treated with Defined Chondrogenic Media versus Chondrogenic Conditioned Media, demonstrates one exemplary embodiment of the novel technology. In this exemplary embodiment, the data demonstrates that this novel approach provides a consistent, reproducible set of factors for differentiation into cartilage. This Chondrogenic Consortia Media shows an enhancement of the differentiation process (FIGS. 10a, 10c).

Conditioned Media from Defined Adipogenic Media vs. Adipogenic Consortia Media from Conditioned Media FIGS. 15a-15e show graphic representations and statistical analysis of one exemplary embodiment of the technology. The figures show secretory factor levels during differentiation of ASCs to fat, with 15(a) ASCs growing in SFM, 15(b) ASCs treated with growth factors (GF) to induce fat differentiation, 15(c) ASCs treated with Adipogenic Consortia Media to induce fat differentiation, 15(d) Statistical analysis showing significant differences between the level of factors from ASCs growing in SFM vs ASCs treated with growth factors, and 15(e) Statistical analysis showing significant differences between the level of factors from conditioned media of ASCs growing in SFM vs. Consortia Media of ASCs treated with Adipogenic Conditioned Media. The results are taken from three independent experiments using Pairwise t-tests (P value).

Figure 16:
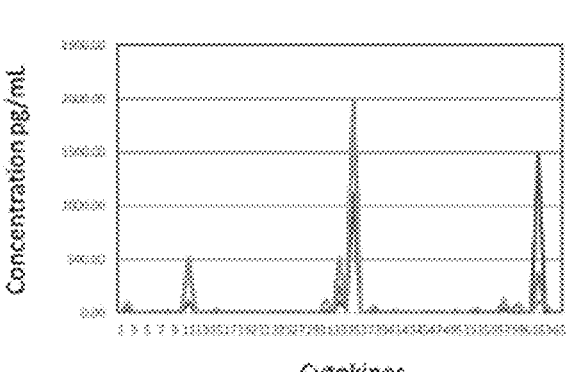
FIG. 16 shows aspects of aspects of factor levels according to exemplary embodiments hereof.

FIG. 16 shows Factor Profiles of ASC's treated with Defined Adipogenic Media versus Adipogenic Conditioned Media, demonstrates one exemplary embodiment of the novel technology. In this exemplary embodiment, the data demonstrates that this novel approach provides a consistent, reproducible set of factors for differentiation into fat. This Adipogenic Consortia Media shows an enhancement of the differentiation process (FIGS. 10*a*, 10*b*).

Plant Cell Cultures and their Combination with Other Plant or Animal Cells

In general plant cell cultures are developed with the plant tissue in culture media with plant growth hormones that de-differentiate plant cuttings, containing differentiated cell types/tissues, to form a totipotent cell mass called a callus which is a meristematic cells. These meristematic cells form the entire plant when grown in growth hormones that can differentiate them to shoot and root systems. Plant cell culture lines are established with plant cells in liquid culture.

In the present exemplary embodiment of this process, two different plant species were co-cultured in the same media, cell #1 and cell #2. The combination two different cells being co-cultured at once, created the Consortia Media. Every 24 hours, for 8 days, samples of the Consortia Media were harvested and analyzed for cell density and total protein concentration.

Figure 17A:
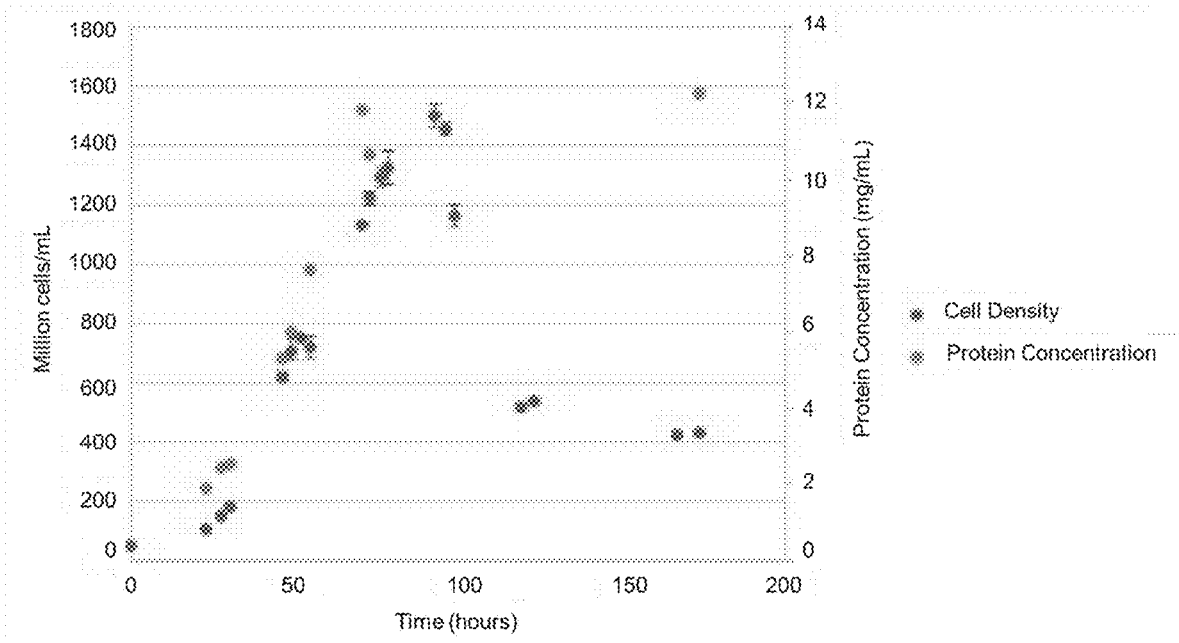
FIGS. 17a-17c show aspects of cell characteristics according to exemplary embodiments hereof.
Figure 17B:
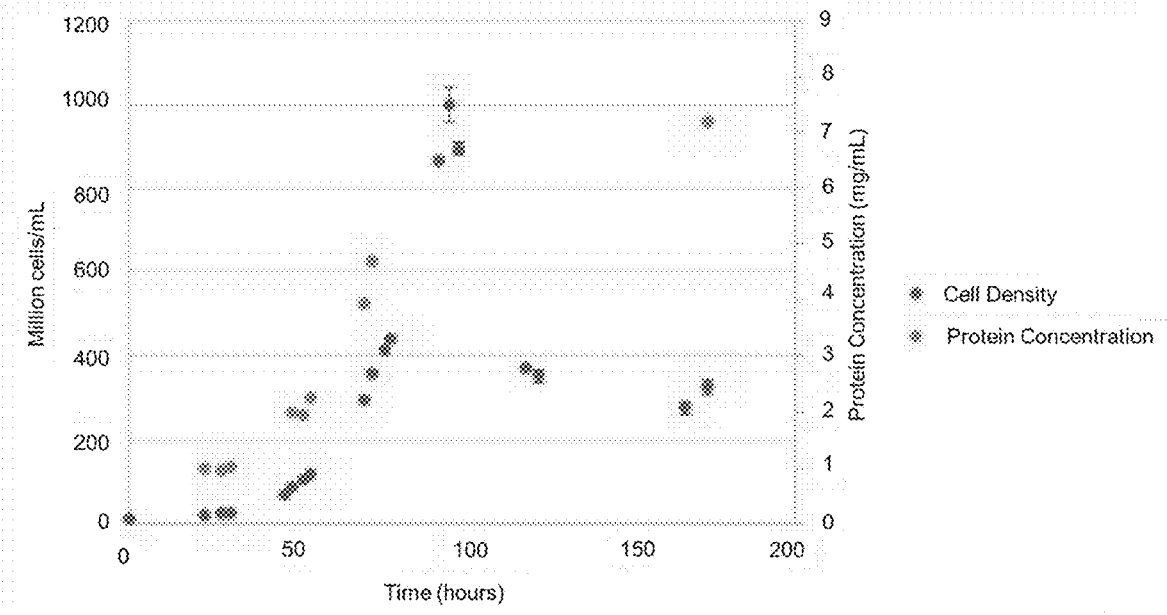
Figure 17C:
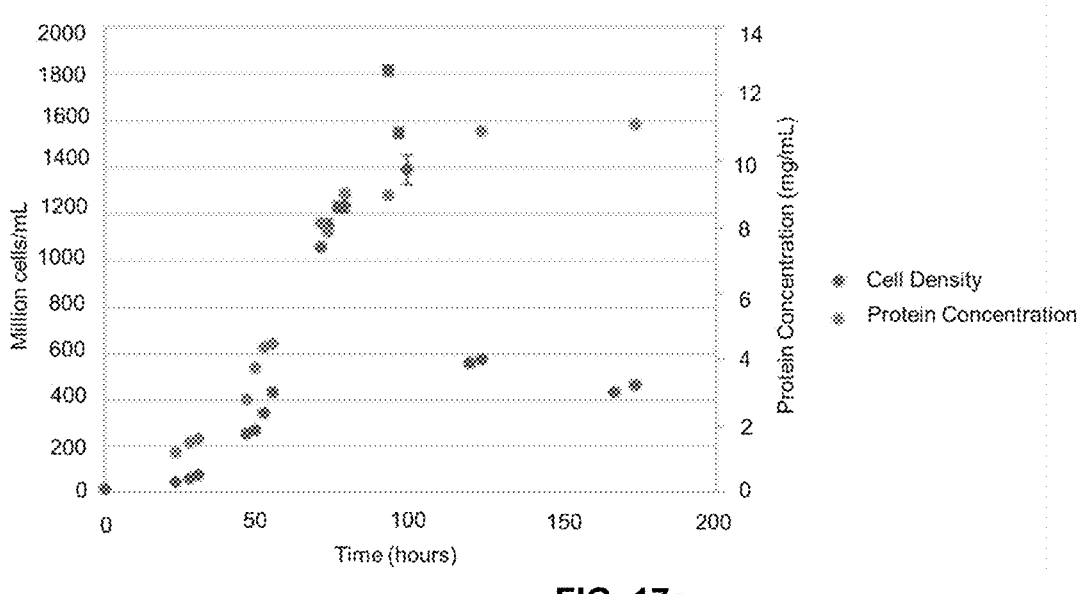
Figure 19A:
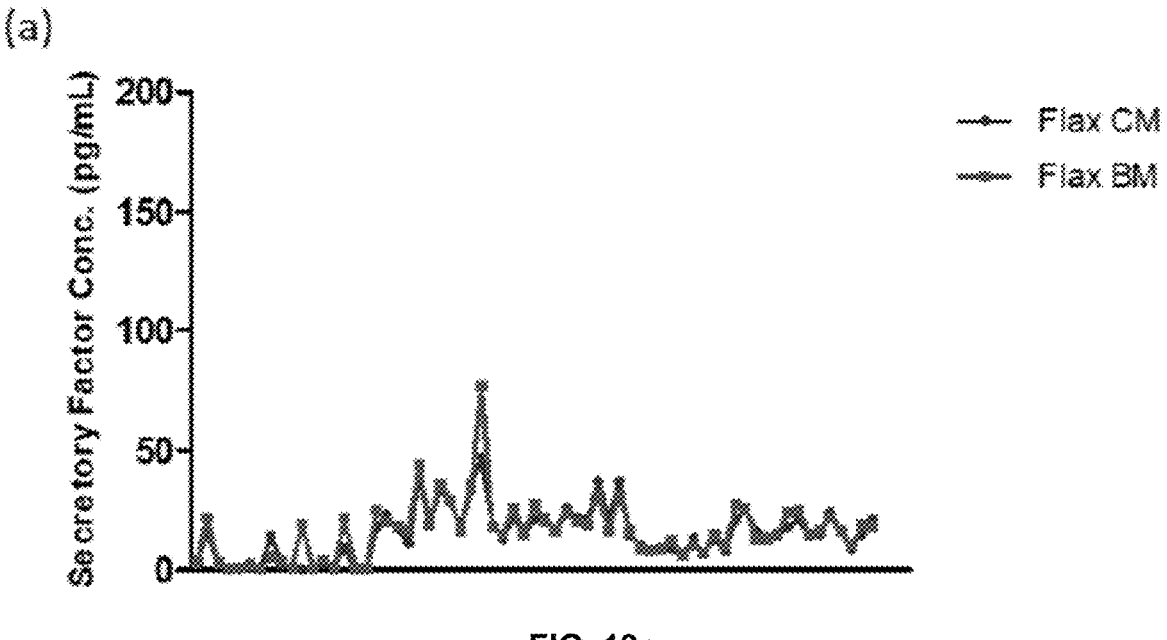
FIGS. 19a-19d show aspects of conditioned media factor profiles according to exemplary embodiments hereof.
Figure 19B:
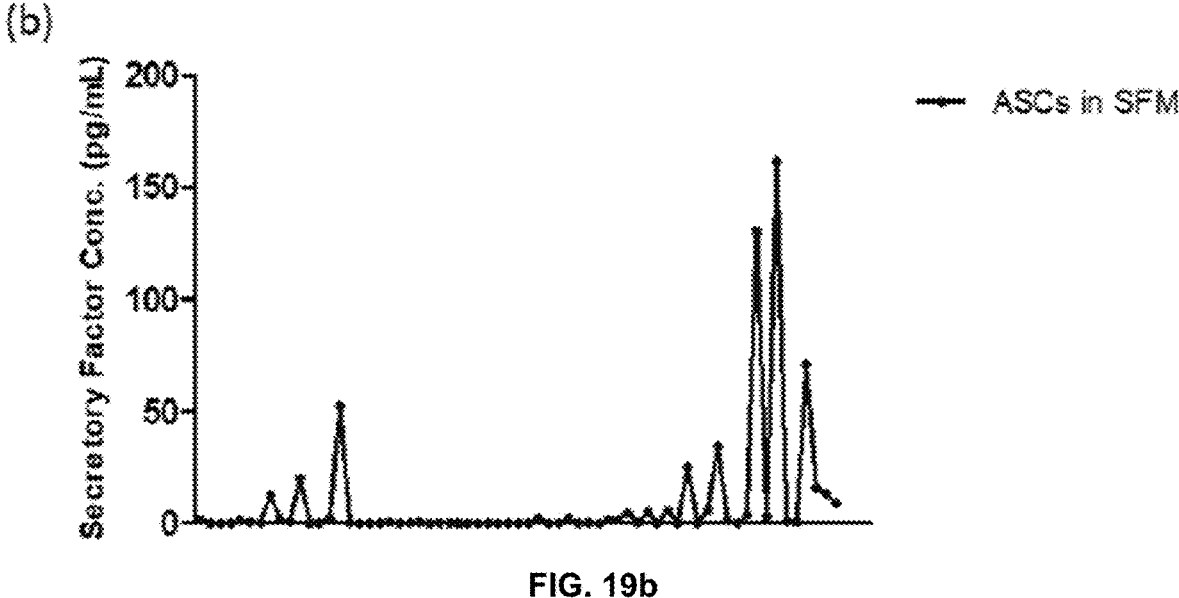
Figure 19C:
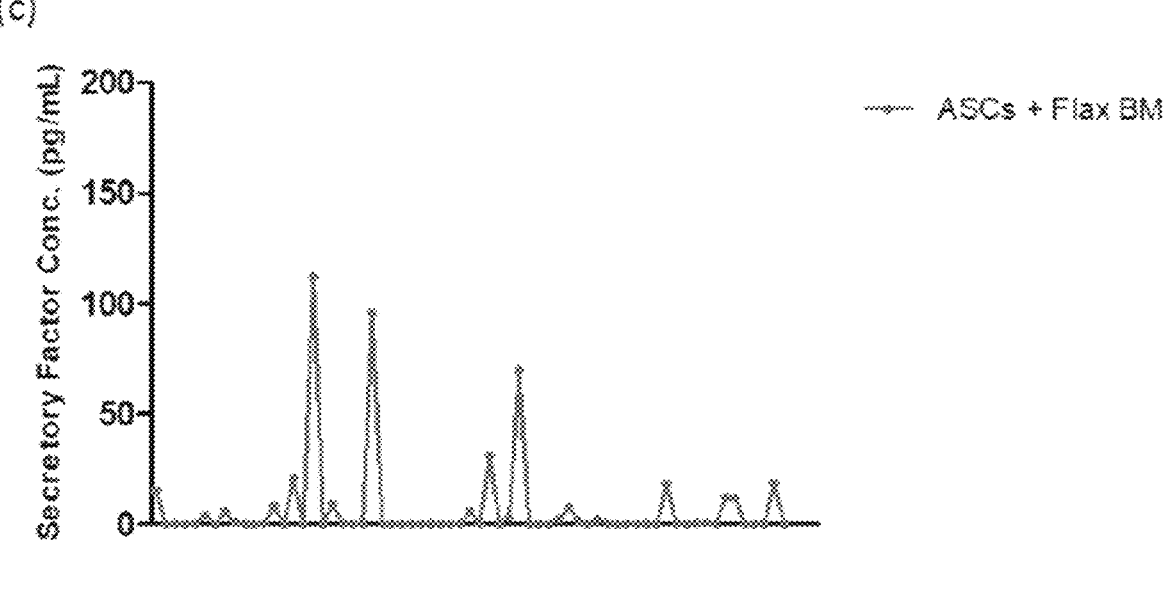
Figure 19D:
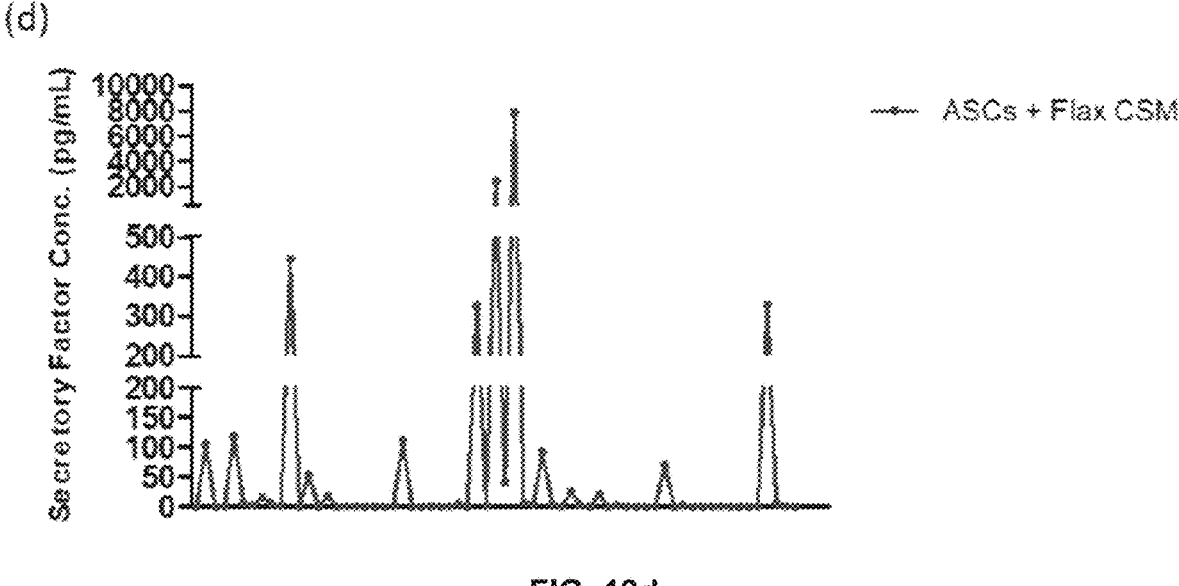
Figure 23:
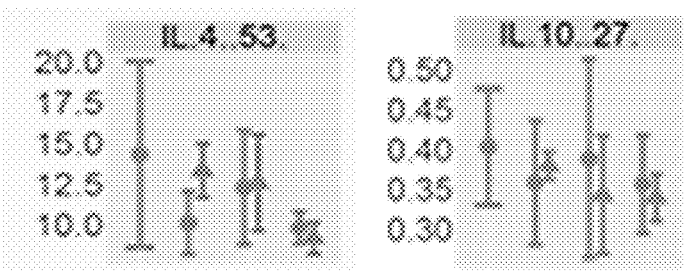
FIG. 23 illustrates the quantification of anti-inflammatory secretory factors in picograms/milliliter (pg/ml) with an immunomicroarray. dots: adipose derived mesenchymal stem cells plated alone; triangles: adipose derived mesenchymal stem cells plated in combination with another set of adipose derived mesenchymal stem cells at the same harvesting age.
Figure 23:
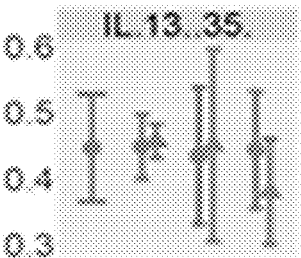
Figure 23:
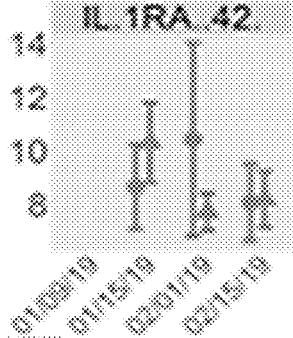
Figure 23:
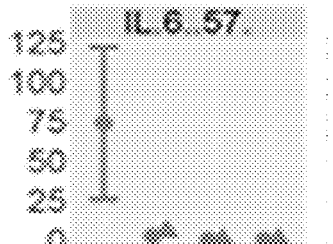
Figure 24:
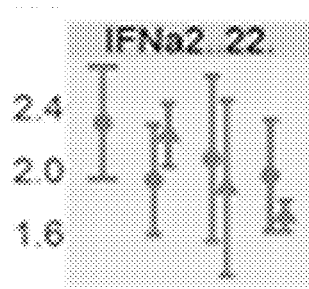
FIG. 24 illustrates the quantification of anti-viral secretory factors in picograms/milliliter (pg/ml) with an immunomicroarray. dots: adipose derived mesenchymal stem cells plated alone; triangles: adipose derived mesenchymal stem cells plated in combination with another set of adipose derived mesenchymal stem cells at the same harvesting age.
Figure 24:
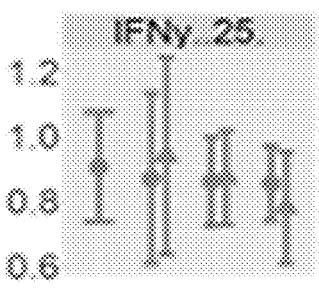
Figure 24:
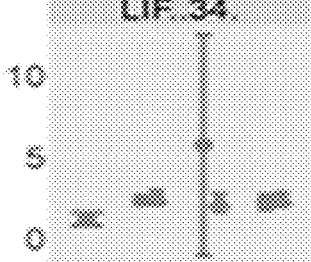
Figures 25A, 25B, 25C, 25D:
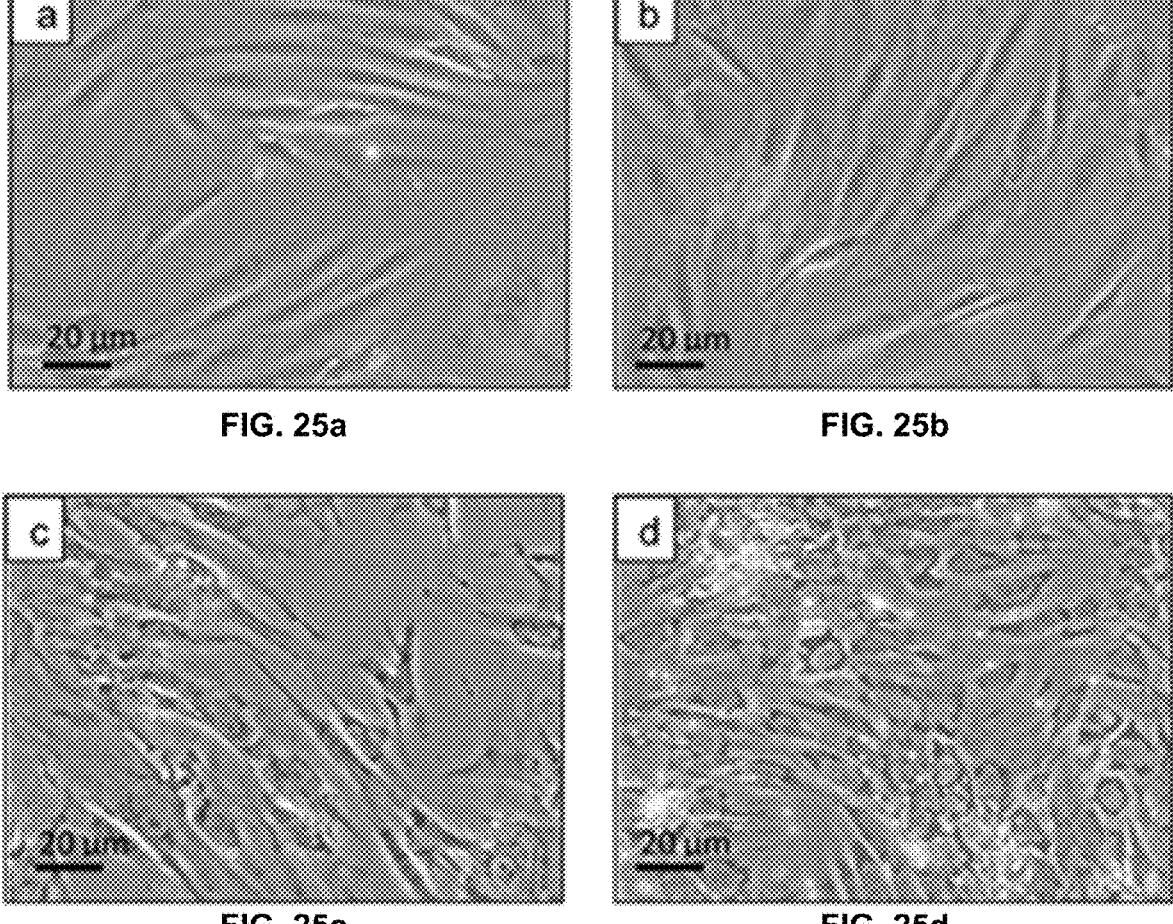
FIGS. 25a-25d shows Human adipose derived mesenchymal stem cells and fibroblast growing in CFx. (a) Human fibroblasts after three days and (b) after 7 days in culture. (c) Adipose derived mesenchymal stem cells after three days and (d) after 7 days in culture.

When compared to cell cultures of cell #1 and cell #2 cultured separately, higher rates of cell density, the growth of cell culture biomass and protein concentration was found in the Consortia Media as demonstrated in FIGS. 17*a*-17*c*.

FIGS. 18*a*-*b* and 18*c*-*d* (Images at 10× and 20× magnification) show ASCs cultured in 6-well plates precoated with fibronectin in SFM+10% HFCM. After 48 hours, the media was replaced for fresh SFBM-112818ACFSF+10% HFCM-012318ACFSF (Human Media—controls) in 3 wells (#1-3) and 2,4-D/KIN media (Plant Media—LMS) in the rest of wells (#4-6). After 72 hours, pictures of the cells were taken before trypsinization. The viability of growing animal cells in plant conditioned media was confirmed as shown in FIG. 21 (TABLE 2). Table 2 shows the viability of growing animal cells in Plant Conditioned Media. In some cultures, the cells were growing in SFBM+10%HFCM and in another cultures, the cells were growing in LMS media.

Human Adipose Stem Cell & Plant Stem Cell Culture in Human Culture Media

Adipose Stem/Stromal Cell Isolation and Culture: Same protocol described before for ASC isolation, culture, and expansion.

Adipose stem cell inoculation into static bottles with Consortia Media from Flax: Same protocol described before for cell inoculation into spinner bottles or bioreactor that contains Fibra-cel disks. In this case Hair differentiation serum-free Consortia Media developed in our laboratory is used for spinner bottles or bioreactor. Adipose Stem Cells were maintained undifferentiated in Serum-free Consortia Media developed in our laboratory.

Adipose Stem/Stromal Cell Inoculation into Static Bottles with Flax Biomass: Flax biomass was growing in Serum-free Consortia Media developed in our laboratory and adipose stem cells were added at a density of $1 \times 10^5$ cells/mL. Then, the consortia media (CSM) was collected after 72 hrs. of cell-cell interactions and evaluated by cytokine multiplex analysis.

Adipose Stem/Stromal Cell Inoculation into Static Bottles with Flax Biomass: Consortia media from Flax was adding to supplement the Serum-free Consortia Media developed in our laboratory. Then, ASCs were added plated at a cell density of $1 \times 10^5$ cells/mL. The consortia media (CSM) was collected after 72 hrs. of cell-cell interactions and evaluated by cytokine multiplex analysis.

FIGS. 19*a*-19*d* show graphic representations of Consortia Media factor profiles. These secretory factor levels were obtained during cell-cell interactions between ASCs and Flax consortia media (Flax CSM) or Flax Biomass (Flax BM) with 19(*a*) Secretory factor profile of Flax CM or Flax BM using human antibodies that cross react with plant secretory factors, 19(*b*) ASCs growing in SFM, 19(*c*) ASCs co-cultured with Flax BM in human culture media, and 19(*d*) ASCs culture with Flax CM (1%) in human culture media.

FIG. 22 (TABLE 3) shows Cytokine multiplex analysis of Consortia media (CSM) obtained from the interactions between human adipose stem and Flax Biomass (Flax-B) or Flax Consortia Media (FlaxCSM). The values correspond to the cytokine level in pg/mL. Table 3 shows that cytokine multiplex analysis was compared to the profile obtained in FlaxCSM (FlaxCSM alone) and various co-culture. In some cultures, the cells were cultured in CSM (ASCs CSM), in other cultures the cells were cultured with Flax-B CSM (ASCs+Flax-B (CSM), and in other culture the cells were cultured in FlaxCSM (ASCs+1% FlaxCM (CSM).

These experiments demonstrate the viability of culturing species in cultured media of other species, thus creating new platforms from which to create novel factor profiles as supported by the previously discussed experiments.

Benefits

Benefits of the exemplary embodiments described herein may include, but are not limited to:

In producing and/or using the Consortia Media/Factors as described above, we have designed a way to have a consistency of factors being produced. This includes the standardization of the processes necessary to formulate treatments for various diseases/conditions, including but not limited to, human, other animals, plants, and agriculture.

In addition, there have been safety and regulatory concerns (both domestically and internationally) on the use of human derived stem cells. The Consortia Factors, including the plant derived Consortia Factors can generate what in effect are the same type of factors (such as polypeptide factors) obtained from human stem cells. The idea is that the factors generated from the Consortia Factors are more efficient at helping consistent differentiation of the stem cells, including into human cells.

By using the Consortia Factors, we are able to use universally ubiquitous sets of physiologically balanced compounds that will allow the recipient's own body to use the compound in a self-limiting manner to self-regenerate/re-new/heal tissues/bone/organs. (This is analogous to giving the body a calcium supplement. The source of the supplement, whether derived from milk, plants, or found as an element in the earth, is irrelevant. What is relevant is giving the patient the calcium. Here what is relevant is not the cell source, but the derivatives i.e. the consortia factors, that produces the desired results).

Agriculture takes tremendous amounts of resources. From land use, to water use, nutrients etc. The process we have developed, particularly with the Consortia Factors enables the growth of agriculture with a fraction of the resources. This is accomplished because we are not actually growing plants, just all the nutrients and byproducts of plants. We can, in essence, grow any plant we want, without actually growing the actual plant. Instead we grow what would be described as a biomass that has all the desired yield of the plant we are not growing. This can result in a food sources, nutritional supplements, medicinal products, Consortia Factors, biofuel, and agricultural products.

The current methodology of deriving stem cells, factors, or Conditioned Media, creates scenarios wherein the profile of the factors and/or cells being produced, are inconsistent, and often unhealthy or have a very short span in which they can be produced or used. In contrast, we are collecting sets of factors from cells that are synchronized and healthy which harmonize the factors, increasing efficacy. Specifically, it will have increased specific activities of factors, such as concentration, types factors, profile of factors, etc. with reasonable consistency (higher than currently attainable).

The conditioned media derived from the cell-cell interactions between human and plan stem cells contains secretory factors that can be used in Regenerative Medicine or Cosmetics.

Cosmetic Applications

The secretory factors are molecules that promote anti-aging effects when applied topically to the skin. Some of these effects are anti-oxidant and can improve the physical appearance of the skin. Factors such as fibroblast growth factors (FGFs) that play a central role for regeneration of a wide variety of tissues including skin by promoting cellular proliferation and differentiation. Other factors that correspond to small molecules such as interferons (IFNα2, IFNγ) are essential for cellular proliferation and they modulate immune responses. In addition, factors such as Eotaxin-1, granulocyte colony-stimulating factor (G-CSF), macrophage colony stimulating factors (M-CSFs), regulated upon activation normal T cell express sequence (RANTES), epithelial neutrophil activating peptide 78 (ENA-78/CXCL5) re-enforced the immunological system and in this way maintain the integrity of the skin. Interleukins correspond to a group of factors that play an essential role to regulate immune and inflammatory responses in the skin and other tissues. Vascular endothelial growth factor (VEGF) in harmony with some of the factors described above, is involved in maintenance of skin function and regeneration as it occurs during wound healing.

These systems may also work to promote hair differentiation (which will in turn lead to hair growth). In using the Consortia Factors (delivered either topically or injected into the scalp) the natural growth of hair may be stimulated. In this application, Consortia Factors, delivered directly or using them in the Conditioned Media they may be produced in, may help trigger cell/tissue/organ regeneration. This may be true for growth in eukaryotic cells, human cells, animal cells, and even plant cells.

Biopharmaceutical Applications

Some effects exerted by these factors may include but are not limited to the promotion of wound healing, angiogenesis, cellular proliferation, cellular survival, anti-aging effects, antioxidant effects, anti-inflammatory effects, osteogenesis, chondrogenesis, adipogenesis, hair regeneration. These factors can also be beneficial for the treatment of auto-immune diseases and for tissue repair after trauma.

Therapeutic Use of Consortia Factor

The anti-inflammatory, anti-viral, and regenerative effects of the secretory factors found in Consortia Factor (CFx) were assessed.

The CFx used in this experiment were obtained from stem cells derived from human adipose tissue and fibroblasts. Adipose tissue was enzymatically digested to yield the stromal vascular fraction (SVF) containing a mixed population of cells, and, high levels of secretory factors mainly from mesenchymal stem cells.

To quantify the amount of anti-inflammatory and anti-viral secretory factors, an immune microarray analysis was performed (Eve Technologies, Calgary, AB Canada). Adipose derived mesenchymal stem cells were plated either alone or in combination with another set of adipose derived mesenchymal stem cells at the same harvesting age; and the CFx in the media were quantified at different time points. The amounts of secretory factors were measured in picograms/milliliter (pg/ml). As illustrated in FIG. 1, where the dots correspond to the amount (average and standard deviation) of secretory factors obtained from individual stem cell lines plated on microcarriers, and where the triangles correspond to a combination of three cell lines also plated on microcarriers, CFx were found to contain major anti-inflammatory factors including interleukin (IL)-1 receptor antagonist, IL-4, IL-6, IL-10, and IL-13. Secretory factors found in CFx are immunoregulatory molecules that control the proinflammatory response. These factors act in concert with inhibitors and soluble molecules to regulate the human immune response.

Figure 2:
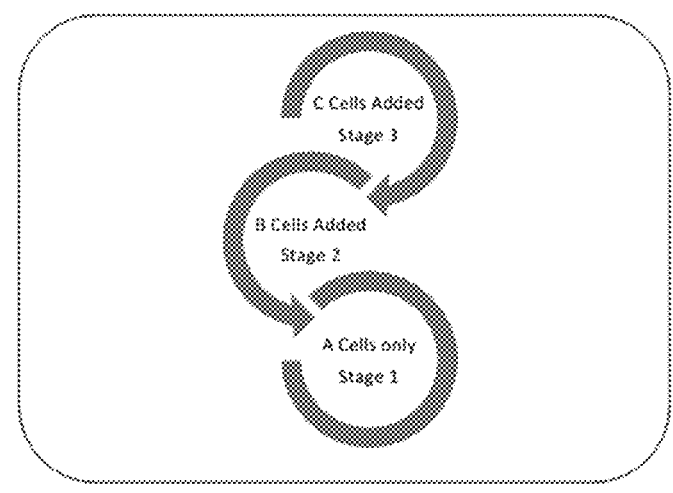
FIG. 2 shows aspects of a culturing technique comprising sequential co-culturing in a same receptacle.

As further illustrated in FIG. 2, where the dots correspond to the amount (average and standard deviation) of secretory factors obtained from individual stem cell lines plated on microcarriers, and where the triangles correspond to a combination of three cell lines also plated on microcarriers, CFx were found to contain major anti-viral factors such as Interferon (IFN)-α2, IFNγ and leukemia inhibitory factor (LIF).

Figure 3:
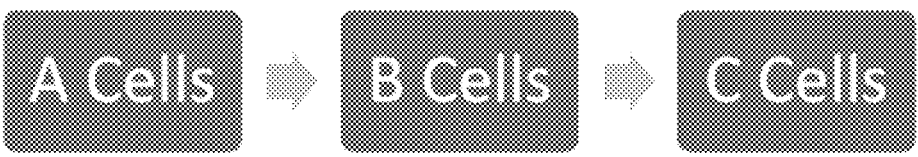
FIG. 3 shows aspects of a culturing technique using sequential a unidirectional system.

To evaluate the efficacy of CFx promotes tissue regeneration, the effects of CFx on Human adipose derived mesenchymal stem cells and fibroblast growth was assessed in vitro. As illustrated in FIG. 3, comparing the growth of Human adipose derived mesenchymal stem cells and fibroblast growing in CFx at 3 and 7 days, it was demonstrated that CFx promoted proliferation of both human fibroblasts and adipose derived mesenchymal stem cells.

The mix of secretory factors released by stem cells following effective cell-cell interactions and consists of soluble factors contained in CFx was found to allow human adipose derived mesenchymal stem cells and fibroblasts to grow in bi- and tri-dimensional cultures. In vitro experiments shown that these secretory factors had enhanced regenerative effects on human skin, hair, and bone, demonstrating that CFx also contained secretory factors essential for cell survival, proliferation, and function.

CFx was also found to contain secretory factors that have anti-viral effects. For instance, IFNs have been approved to treat some viral diseases. IFNs work to inhibit the replication of a wide range of DNA and RNA animal viruses. They can disrupt several different stages of viral development including the synthesis of viral polypeptides, and viral gene transcription. LIF, another factor found in CFx, can inhibit HIV infection of human placental tissue in a dose-dependent manner.

Additionally, CFx was found to contain secretory factors that have anti-inflammatory effects. For instance, IL-1RA is a competitive inhibitor that binds to IL-1α and IL-1β preventing them from inducing a pro-inflammatory response. IL-10 has been shown to exert anti-inflammatory effects by reducing the activity of some lymphocytes that amplify the inflammatory response and is considered a key immunoregulator in viral, bacterial, fungal, protozoan and helminth infections. IL-13 can suppress inflammatory responses by regulating macrophages to inhibit their production of proinflammatory factors such as TNFα and IL-8. IL-4 also has anti-inflammatory properties; specifically, the ability to suppress the production of tumor necrosis factor (TNF)-α and IL-1β by activated human monocytes. IL-6 has both anti- and pro-inflammatory effects depending on the intracellular cascades activated. When IL-6 binds to its specific cell surface receptor to induces its classical intracellular signaling pathway, it functions mainly as an anti-inflammatory and regenerative factor.

Therefore, the use of CFx that contain a combination of physiologically balanced set of factors can help drive the in vivo signaling towards the desired anti-inflammatory and antiviral action on the cellular level and can result in very rapid clinical improvement.

Where a process is described herein, those of ordinary skill in the art will appreciate that the process may operate without any user intervention. In another embodiment, the process includes some human intervention (e.g., a step is performed by or with the assistance of a human).

As used herein, including in the claims, the phrase "at least some" means "one or more," and includes the case of only one. Thus, e.g., the phrase "at least some ABCs" means "one or more ABCs", and includes the case of only one ABC.

As used herein, including in the claims, term "at least one" should be understood as meaning "one or more", and therefore includes both embodiments that include one or multiple components. Furthermore, dependent claims that refer to independent claims that describe features with "at least one" have the same meaning, both when the feature is referred to as "the" and "the at least one".

As used in this description, the term "portion" means some or all. So, for example, "A portion of X" may include some of "X" or all of "X". In the context of a conversation, the term "portion" means some or all of the conversation.

As used herein, including in the claims, the phrase "using" means "using at least," and is not exclusive. Thus, e.g., the phrase "using X" means "using at least X." Unless specifically stated by use of the word "only", the phrase "using X" does not mean "using only X."

As used herein, including in the claims, the phrase "based on" means "based in part on" or "based, at least in part, on," and is not exclusive. Thus, e.g., the phrase "based on factor X" means "based in part on factor X" or "based, at least in part, on factor X." Unless specifically stated by use of the word "only", the phrase "based on X" does not mean "based only on X."

In general, as used herein, including in the claims, unless the word "only" is specifically used in a phrase, it should not be read into that phrase.

As used herein, including in the claims, the phrase "distinct" means "at least partially distinct." Unless specifically stated, distinct does not mean fully distinct. Thus, e.g., the phrase, "X is distinct from Y" means that "X is at least partially distinct from Y," and does not mean that "X is fully distinct from Y." Thus, as used herein, including in the claims, the phrase "X is distinct from Y" means that X differs from Y in at least some way.

It should be appreciated that the words "first" and "second" in the description and claims are used to distinguish or identify, and not to show a serial or numerical limitation. Similarly, the use of letter or numerical labels (such as "(a)", "(b)", and the like) are used to help distinguish and/or identify, and not to show any serial or numerical limitation or ordering.

As used herein, including in the claims, the terms "multiple" and "plurality" mean "two or more," and include the case of "two." Thus, e.g., the phrase "multiple ABCs," means "two or more ABCs," and includes "two ABCs." Similarly, e.g., the phrase "multiple PQRs," means "two or more PQRs," and includes "two PQRs."

The present invention also covers the exact terms, features, values and ranges, etc. in case these terms, features, values and ranges etc. are used in conjunction with terms such as about, around, generally, substantially, essentially, at least etc. (i.e., "about 3" shall also cover exactly 3 or "substantially constant" shall also cover exactly constant).

As used herein, including in the claims, singular forms of terms are to be construed as also including the plural form and vice versa, unless the context indicates otherwise. Thus, it should be noted that as used herein, the singular forms "a," "an," and "the" include plural references unless the context clearly dictates otherwise.

Throughout the description and claims, the terms "comprise", "including", "having", and "contain" and their variations should be understood as meaning "including but not limited to" and are not intended to exclude other components unless specifically so stated.

It will be appreciated that variations to the embodiments of the invention can be made while still falling within the scope of the invention. Alternative features serving the same, equivalent or similar purpose can replace features disclosed in the specification, unless stated otherwise. Thus, unless stated otherwise, each feature disclosed represents one example of a generic series of equivalent or similar features.

The present invention also covers the exact terms, features, values and ranges, etc. in case these terms, features, values and ranges etc. are used in conjunction with terms such as about, around, generally, substantially, essentially, at least etc. (i.e., "about 3" shall also cover exactly 3 or "substantially constant" shall also cover exactly constant).

Use of exemplary language, such as "for instance", "such as", "for example" ("e.g.,") and the like, is merely intended to better illustrate the invention and does not indicate a limitation on the scope of the invention unless specifically so claimed.

This patent document contains material subject to copyright protection. The copyright owner has no objection to the reproduction of this patent document or any related materials in the files of the United States Patent and Trademark Office, but otherwise reserves all copyright whatsoever.

While the invention has been described in connection with what is presently considered to be the most practical and preferred embodiments, it is to be understood that the invention is not to be limited to the disclosed embodiment, but on the contrary, is intended to cover various modifications and equivalent arrangements included within the spirit and scope of the appended claims.

We claim:

1. A method of treating lung inflammation and/or coronavirus-induced severe acute respiratory syndrome (SARS-CoV) in a subject comprising:
(i) culturing fibroblast cells in a first media to produce a first conditioned media;
(ii) culturing stem cells in successive inoculations in a three-dimensional scaffold in a second media comprising the first conditioned media to produce a second conditioned media, wherein the stem cells are cultured in a dynamic system, thereby producing a composition comprising the second conditioned media; and
(iii) administering to the subject an aerosolized pharmaceutical composition comprising the composition produced in (ii) using an inhaler or a nebulizer, thereby treating the lung inflammation and/or SARS-CoV in the subject.

2. The method of claim 1, wherein the stem cells are adipose tissue derived stem cells.

3. The method of claim 1, wherein the stem cells and the fibroblast cells are isolated from a same donor, wherein the stem cells are isolated at a first time and the fibroblasts are isolated at a second time, and wherein the first time and the second time are different times.

4. The method of claim 1, wherein the stem cells and the fibroblast cells are isolated from a different donor.

5. The method of claim 3 or 4, wherein the donor is a human donor.

6. The method of claim 1, wherein the inhaler is a pressurized metered-dose inhaler.

7. The method of claim 1, wherein the SARS-COV is caused by COVID-19.

8. The method of claim 1, wherein the aerosolized pharmaceutical composition comprises an anti-inflammatory factor selected from the group consisting of interleukin (IL)-1 receptor antagonist (IL-1RA), IL-4, IL-6, IL-10, and IL-13, and/or an anti-viral factor selected from the group consisting of interferon (IFN)-$\alpha$2, IFN$\gamma$ and leukemia inhibitory factor (LIF).

9. The method of claim 1, wherein the aerosolized pharmaceutical composition reaches an affected respiratory mucosa to decrease lung inflammation, to decrease viral load and/or to promote tissue regeneration.

10. The method of claim 1, wherein the nebulizer is an atomizer jet nebulizer, a compressor nebulizer, an ultrasonic nebulizer or a mesh nebulizer.

11. The method of claim 1, wherein culturing stem cells in successive inoculations comprises:

(i) culturing a first stem cell isolated from a first donor with a second stem cell isolated from a second donor, wherein the first and the second stem cell have the same harvesting age, or (ii) culturing a first stem cell isolated from a donor at a first time with a second stem cell isolated from the donor at a second time, wherein the first and the second time are different.

12. The method of claim 1, wherein the aerosolized pharmaceutical composition comprises IFN$\gamma$.

13. The method of claim 1, wherein the second media is a serum-free media.

14. A method of decreasing lung inflammation, decreasing viral load, and/or promoting tissue regeneration in a subject comprising:

(i) culturing fibroblast cells in a first media to produce a first conditioned media;

(ii) culturing stem cells in successive inoculations in a three-dimensional scaffold in a second media comprising the first conditioned media to produce a second conditioned media, wherein the stem cells are cultured in a dynamic system, thereby producing a composition comprising the second conditioned media; and (iii) administering to the subject an aerosolized pharmaceutical composition comprising the composition produced in (ii), wherein the subject has a coronavirus-induced severe acute respiratory syndrome (SARS-CoV), thereby decreasing lung inflammation, decreasing viral load, and or promoting tissue regeneration in the subject.

15. The method of claim 14, wherein administering the aerosolized pharmaceutical composition to the subject is by inhalation or by nebulization.

16. The method of claim 14, wherein culturing stem cells in successive inoculations comprises:

(i) culturing a first stem cell isolated from a first donor with a second stem cell isolated from a second donor, wherein the first and the second stem cell have the same harvesting age, or (ii) culturing a first stem cell isolated from a donor at a first time with a second stem cell isolated from the donor at a second time, wherein the first and the second time are different.

17. The method of claim 14, wherein the second media is a serum-free media.

* * * * *